United States Patent
Adachi

(10) Patent No.: US 9,885,798 B2
(45) Date of Patent: Feb. 6, 2018

(54) FOREIGN MATTER DETECTION DEVICE

(71) Applicant: Panasonic Intellectual Property Management Co., Ltd., Osaka (JP)

(72) Inventor: Kazuhiro Adachi, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 15/504,053

(22) PCT Filed: Oct. 23, 2015

(86) PCT No.: PCT/JP2015/005336
§ 371 (c)(1),
(2) Date: Feb. 15, 2017

(87) PCT Pub. No.: WO2016/067575
PCT Pub. Date: May 6, 2016

(65) Prior Publication Data
US 2017/0276820 A1    Sep. 28, 2017

(30) Foreign Application Priority Data
Oct. 31, 2014    (JP) ................... 2014-223730

(51) Int. Cl.
*H02J 17/00* (2006.01)
*G01V 3/08* (2006.01)
(Continued)

(52) U.S. Cl.
CPC .............. *G01V 3/08* (2013.01); *G01N 27/82* (2013.01); *G01V 3/104* (2013.01); *G01V 9/002* (2013.01); *G08B 13/24* (2013.01); *H02J 50/60* (2016.02)

(58) Field of Classification Search
CPC ........... H02J 50/60; G01V 3/08; G01V 3/104; G01V 9/002; G01N 27/82; G08B 13/24
See application file for complete search history.

(56) References Cited

U.S. PATENT DOCUMENTS

| 2013/0241300 A1 | 9/2013 | Miyamoto | |
| 2013/0241302 A1* | 9/2013 | Miyamoto | H02J 50/12 307/104 |

(Continued)

FOREIGN PATENT DOCUMENTS

| JP | 2012-075200 | 4/2012 |
| JP | 2013-192391 | 9/2013 |

(Continued)

OTHER PUBLICATIONS

International Search Report of PCT application No. PCT/JP2015/005336 dated Jan. 12, 2016.

*Primary Examiner* — Daniel Cavallari
(74) *Attorney, Agent, or Firm* — Seed IP Law Group LLP

(57) ABSTRACT

A foreign matter detection device is mounted on a non-contact power supply system that supplies power in a non-contact manner from a power supply unit to a power reception unit. The foreign matter detection device includes a magnetic field sensor and a magnetic field generation unit. The magnetic field sensor detects an amount of magnetic flux that changes due to foreign matter existing between the power supply unit and the power reception unit. The magnetic field generation unit is provided separately from the power supply unit and the power reception unit, includes a magnetic field generation coil unit, and generates a magnetic field for driving the magnetic field sensor.

20 Claims, 22 Drawing Sheets

(51) Int. Cl.
*G01V 3/10* (2006.01)
*G08B 13/24* (2006.01)
*G01N 27/82* (2006.01)
*G01V 9/00* (2006.01)
*H02J 50/60* (2016.01)

(56) References Cited

U.S. PATENT DOCUMENTS

2014/0015329 A1 1/2014 Widmer et al.
2014/0015522 A1 1/2014 Widmer et al.

FOREIGN PATENT DOCUMENTS

| | | |
|---|---|---|
| JP | 2015-204707 | 11/2015 |
| JP | 2015-211536 | 11/2015 |
| WO | 2014/011776 | 1/2014 |

\* cited by examiner

FOREIGN MATTER DETECTION DEVICE

TECHNICAL FIELD

The present disclosure relates to a foreign matter detection device.

BACKGROUND ART

A non-contact power supply system is a system for receiving AC current from a power supply side in a non-contact manner at a power reception side by electromagnetic induction, and application has been studied for a system that supplies power in a non-contact manner from a ground side to a drive motor during parking.

In particular, in the non-contact power supply system applied for a power supply method to a mobile body, there is a problem that foreign matter mixed into the non-contact power supply system becomes a heating element. Specifically, when foreign matter is mixed between a power supply coil and a power reception coil, foreign matter such as a metal or a magnetic substance may be heated due to magnetic flux passing through the foreign matter.

Patent Literature 1 discloses a foreign matter detection device for sensing foreign matter existing near a sensing coil without newly providing a sensor. Specifically, presence of foreign matter is determined by detecting an electrical change in the sensing coil that due to the foreign matter.

CITATION LIST

Patent Literature

PTL 1: Unexamined Japanese Patent Publication No. 2013-192391

SUMMARY OF THE INVENTION

The present disclosure provides a foreign matter detection device having high foreign matter detection sensitivity without depending on an external magnetic field environment.

The foreign matter detection device according to an exemplary embodiment of the present disclosure is mounted on a non-contact power supply system that supplies power in a non-contact manner from a power supply unit to a power reception unit. The foreign matter detection device includes a magnetic field sensor and a magnetic field generation unit. The magnetic field sensor detects an amount of magnetic flux that changes due to foreign matter existing between the power supply unit and the power reception unit. The magnetic field generation unit is provided separately from the power supply unit and the power reception unit, includes a magnetic field generation coil unit, and generates a magnetic field for driving the magnetic field sensor.

The foreign matter detection device of the present disclosure drives the magnetic field sensor by using the magnetic field generation unit provided separately from the power supply unit and the power reception unit. Thus, the foreign matter detection device can have high foreign matter detection sensitivity without depending on the external magnetic field environment.

DESCRIPTION OF EMBODIMENTS

Figure 1:
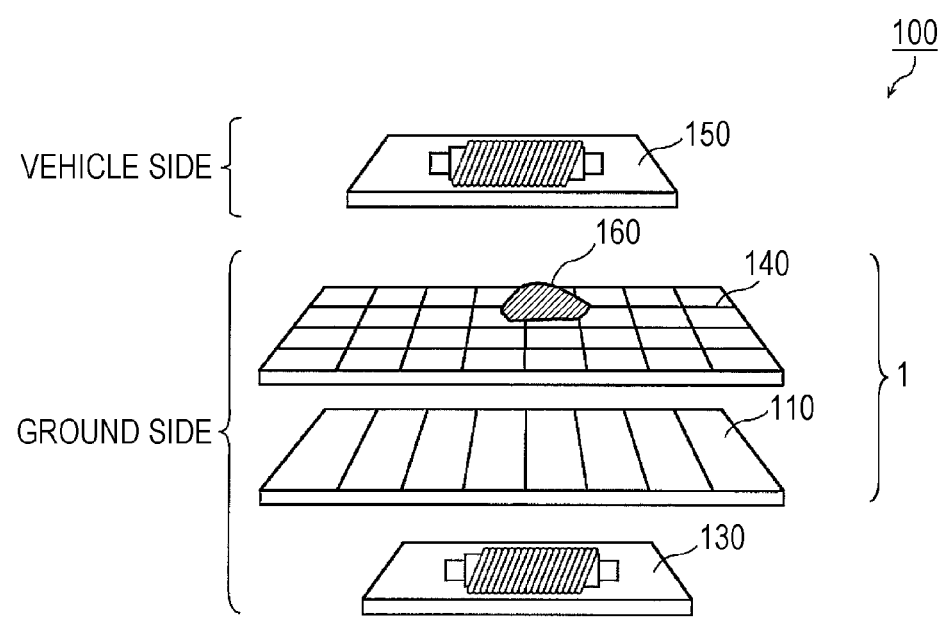
FIG. 1 is a schematic configuration diagram of a non-contact power supply device including a foreign matter detection device according to an exemplary embodiment.

Prior to a description of exemplary embodiments of the present invention, a problem in a conventional foreign matter detection device is described briefly. The foreign matter detection device according to the above described conventional technique is targeted to a field of mobile device application. In such a device, since an inductance of a power supply coil is large, an amount of change in magnetic flux caused by foreign matter is very small compared to the entire amount of magnetic flux. Therefore, in a case the device is applied to a high-power supply system such as that for automobiles, detecting foreign matter is difficult.

In the following, a foreign matter detection device according to the exemplary embodiments of the present disclosure is described in detail with reference to the drawings. Each of the exemplary embodiments described below illustrates a preferred specific example of the present invention. Therefore, values, shapes, materials, components, arrangement and connection form of the components, and the like illustrated in the following exemplary embodiments are examples, and are not intended to limit the present invention. Accordingly, out of the components in the following exemplary embodiments, components not described in an independent claim showing the most significant concept of the present invention are described as arbitrary components.

The drawings are schematic diagrams, and are not necessarily illustrated exactly. In the drawings, the same constituent members are denoted by the same reference numerals.

First Exemplary Embodiment

[1. Overall Configuration of Non-Contact Power Supply Device]

FIG. 1 is a schematic configuration diagram of a non-contact power supply device including a foreign matter detection device according to an exemplary embodiment. Non-contact power supply device 100 illustrated in FIG. 1 has power supply coil substrate 130, power reception coil substrate 150, magnetic field generation coil substrate 110, and sensor coil substrate 140.

Power supply coil substrate 130 is a power supply unit having a power supply coil, and is installed at a ground side, for example. Power reception coil substrate 150 is a power reception unit having a power reception coil, and is disposed at a mobile body, for example. Power supply coil substrate 130 generates a magnetic field for power transmission by AC power supplied to the power supply coil. Power reception coil substrate 150 receives the above AC power by electromagnetic induction by receiving the magnetic field for power transmission generated by power supply coil substrate 130 using the power reception coil. With this configuration, power reception coil substrate 150 is capable of receiving power from power supply coil substrate 130 in a non-contact manner.

For example, foreign matter 160 existing between power supply coil substrate 130 and power reception coil substrate 150 and on a road at which power supply coil substrate 130 is disposed, may become a heating element by absorbing energy of the magnetic field for power transmission generated from power supply coil substrate 130. From this, foreign matter 160 has a possibility to become a dangerous object by being in contact with a human.

Sensor coil substrate 140 is a substrate for detecting foreign matter 160 existing between power supply coil substrate 130 and power reception coil substrate 150, to collect foreign matter 160 described above. Specifically, sensor coil substrate 140 has a sensor coil that is a magnetic field sensor, and detects a change in an amount of magnetic flux in the sensor coil due to presence of foreign matter 160, as a voltage change in the sensor coil.

Magnetic field generation coil substrate 110 has a magnetic field generation coil for driving the sensor coil. Specifically, a magnetic field generated by the magnetic field generation coil of magnetic field generation coil substrate 110 is applied to the sensor coil of sensor coil substrate 140. Magnetic field generation coil substrate 110 and sensor coil substrate 140 configure foreign matter detection device 1 for detecting foreign matter 160.

Here, sensor coil substrate 140 is capable of detecting a magnetic flux change in the sensor coil due to presence of foreign matter 160 by receiving the magnetic field for power transmission generated from power supply coil substrate 130 or power reception coil substrate 150 each of which is a main component of the non-contact power supply device. However, in a case the non-contact power supply device is applied for automobiles, since an inductance of the power supply coil is large, an amount of change in magnetic flux caused by foreign matter 160 is very small compared to the entire amount of magnetic flux. For this reason, detecting foreign matter 160 may be difficult.

On the other hand, non-contact power supply device 100 according to the present exemplary embodiment separately has magnetic field generation coil substrate 110, in addition to power supply coil substrate 130 and power reception coil substrate 150. Magnetic field generation coil substrate 110 is a magnetic field generation unit that generates the magnetic field for driving the sensor coil for detecting the amount of magnetic flux that changes due to foreign matter 160, and is provided separately from power supply coil substrate 130 and power reception coil substrate 150. From this, foreign matter detection sensitivity is improved. By adding magnetic field generation coil substrate 110, a magnetic field distribution can be arbitrarily generated in which sensor coil substrate 140 is capable of detecting foreign matter with high sensitivity without depending on a magnetic field distribution generated by power supply coil substrate 130 and power reception coil substrate 150. Alternatively, a magnetic field distribution of magnetic field generation coil substrate 110 can be arbitrarily generated to complement ununiformity of the magnetic field distribution generated by power supply coil substrate 130 and power reception coil substrate 150.

In non-contact power supply device 100 illustrated in FIG. 1, sensor coil substrate 140 is disposed above magnetic field generation coil substrate 110; however, sensor coil substrate 140 may be disposed below magnetic field generation coil substrate 110.

Sensor coil substrate 140 and magnetic field generation coil substrate 110 may be disposed at a mobile body side, not the ground side.

Foreign matter detection device 1 is capable of detecting not only conductive foreign matter, but also even an insulator having magnetism.

[1-1. Power Supply from Power Supply Coil to Magnetic Field Generation Coil]

Figure 2:
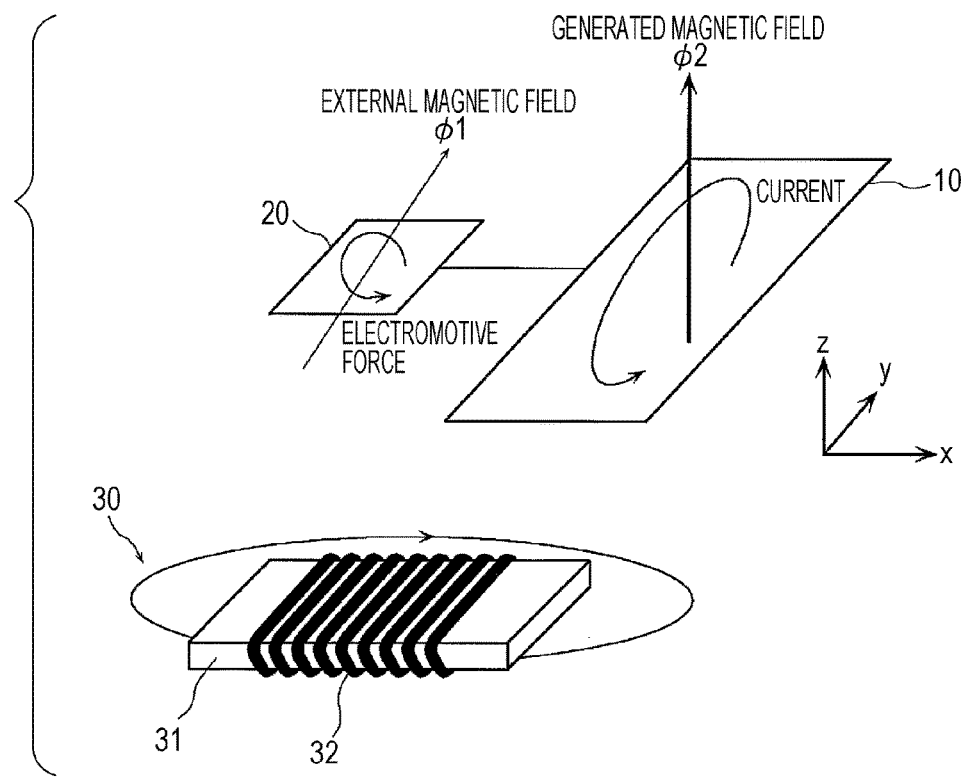
FIG. 2 is a diagram representing an example of a relationship between a magneto coil and a magnetic field generation coil.

FIG. 2 is a diagram representing an example of a relationship between a magneto coil and a magnetic field generation coil. FIG. 2 represents a connection relationship between magnetic field generation coil 10 and magneto coil 20. FIG. 2 illustrates solenoid type power supply coil 30. Power supply coil 30 has core 31 and winding wire 32. X, y, z directions of FIG. 2 is a three-dimensional orthogonal coordinate system. A horizontal plane of power supply coil 30 is defined by the x direction and the y direction (xy plane), and a vertical direction (normal line direction) orthogonal to the horizontal plane is defined as the z direction. The x direction is a direction along a central axis of winding wire 32 of power supply coil 30.

In a solenoid coil or a spiral coil used as a coil for power transmission, a location exists in which a magnetic field in the z direction is zero. For example, in a case of power supply coil 30 illustrated in FIG. 2, a region exists in which magnetic field in the z direction Hz is zero near the center in x direction of power supply coil 30. That is, magnetic flux in the z direction is zero. Since sensor coil substrate 140 and the sensor coil disposed thereon are disposed in parallel to the xy plane of power supply coil 30, a magnetic flux direction passing through the sensor coil is the z direction. That is, the detection sensitivity to foreign matter 160 is reduced in a region in which the magnetic flux in the z direction does not exist.

To solve the above problem, magnetic field generation coil 10 is provided for generating the magnetic flux in the z direction to complement the magnetic flux distribution in the z direction generated by power supply coil 30. As illustrated in FIG. 2, in a case magnetic field generation coil 10 is formed to be parallel to the xy plane, the magnetic flux in the z direction can be generated when current is caused to flow through magnetic field generation coil 10. Here, to cause the current to flow through magnetic field generation coil 10, it is necessary to connect a power source to magnetic field generation coil 10. Magneto coil 20 is provided as the power source of magnetic field generation coil 10. Magneto coil 20 is capable of generating power by electromagnetic induction by being disposed at a location in which the magnetic flux in the z direction exists, in the magnetic flux distribution of power supply coil 30. In FIG. 2, magneto coil 20 is not disposed near the center in x direction of power supply coil 30, but is disposed near a boundary between winding wire 32 and an end portion of core 31 of power supply coil 30, in which the winding wire 32 is not wound. Near the boundary, a magnetic flux density in the z direction is large, and power generation efficiency is excellent.

That is, the power generated by magneto coil 20 is supplied as a part or entire of the power source of foreign matter detection device 1. For example, the power can be applied not only as a power source of a drive circuit of magnetic field generation coil 10, but also as power used for a power source of a gate driver, a power source of a microprocessor, a power source of a determination, and communication.

From this, magnetic field generation coil 10, magneto coil 20, and wire connections thereof can be implemented by only simple wiring lines, and other electrical parts are not necessary in principle. Magnetic field generation coil 10, magneto coil 20, and wire connections thereof can be disposed on sensor coil substrate 140. Therefore, regarding that magnetic field generation coil 10 is provided separately, an increase is little in size and weight of non-contact power supply device 100, and it can be implemented at low cost.

When a magnetic coupling coefficient between power supply coil 30 and magneto coil 20 is greater than 10%, a problem may occur in supplying power from power supply coil substrate 130 to power reception coil substrate 150. Accordingly, the magnetic coupling coefficient between magnetic field generation coil 10 and power supply coil 30 is preferably 10% or less.

For a similar reason, a magnetic coupling coefficient between magnetic field generation coil 10 and the power reception coil is also preferably 10% or less.

[1-2. Complement of Magnetic Flux by Magnetic Field Generation Coil]

Figure 3:
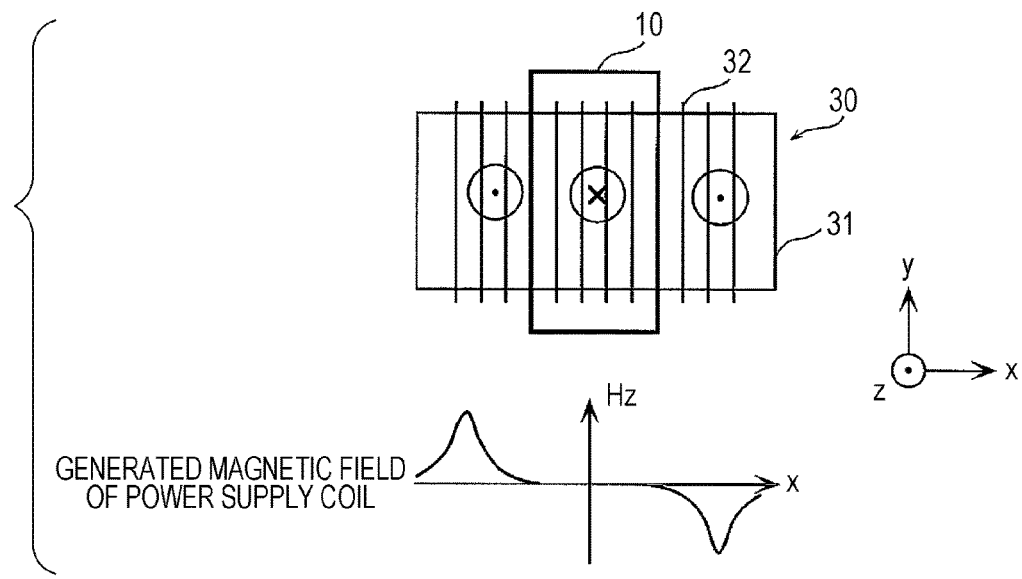
FIG. 3 is a diagram illustrating an example of an arrangement relationship between the magnetic field generation coil and a power supply coil according to the exemplary embodiment.

FIG. 3 is a diagram illustrating an example of an arrangement relationship between the magnetic field generation coil and a power supply coil according to the exemplary embodiment. The lower part of FIG. 3 represents a magnetic field distribution in the z direction of solenoid type power supply coil 30. The generated magnetic field in the central region in the x direction is zero. In foreign matter detection of sensor coil substrate 140 using only the generated magnetic field from power supply coil 30, the detection sensitivity is low in the central region in the x direction. To improve the low detection sensitivity, in the upper part of FIG. 3, magnetic field generation coil 10 is disposed at the central region in the x direction of power supply coil 30. That is, magnetic field generation coil 10 is disposed at a location in which a magnetic field component is relatively small or zero in a normal line direction (z axis direction) of a plane including magnetic field generation coil 10, out of a magnetic field formed by power supply coil 30 and the power reception coil. From this, foreign matter detection sensitivity is improved in the central region in the x direction, and foreign matter can be detected with high accuracy in the entire region on power supply coil 30.

In a case the power supply coil is that of a spiral type, since magnetic field in the z direction is small in a region near the middle point of a straight line connecting the coil center and the coil outermost circumference to each other, the magnetic field generation coil is preferably disposed at the region.

When the power transmission coil is configured by a combination of a spiral type coil and a solenoid type coil, it is sufficient to select a shape of the magnetic field generation coil suitable for a shape of each power transmission coil. In a case of a shape of a power transmission coil other than the solenoid type and spiral type, it is sufficient to select a shape of a magnetic field generation coil suitable for the shape of the power transmission coil.

[2. Configuration of Magnetic Field Generation Coil]

As described above, the magnetic field generated by the magnetic field generation coil is used as an external magnetic field used by the sensor coil. Hereinafter, a configuration is exemplified of the magnetic field generation coil according to the present exemplary embodiment.

Figure 4A:
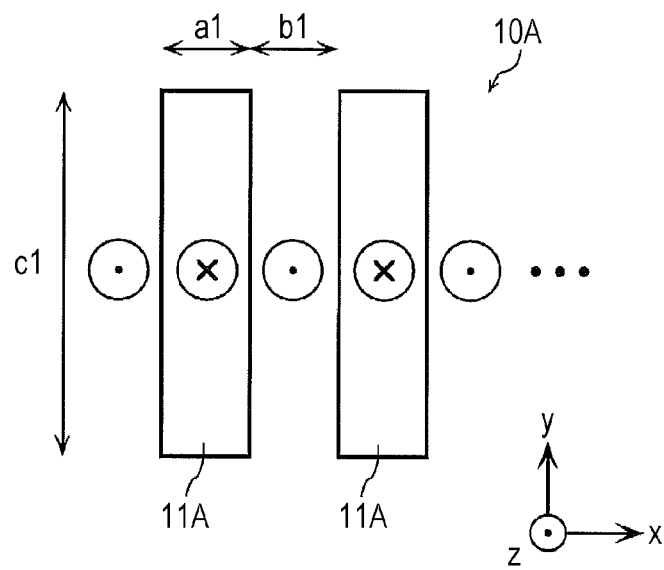
FIG. 4A is a plan view illustrating an example of a shape of the magnetic field generation coil according to the exemplary embodiment.

FIG. 4A is a plan view illustrating an example of a shape of the magnetic field generation coil according to the exemplary embodiment. Magnetic field generation coil 10A represented in FIG. 4A is provided on magnetic field generation coil substrate 110 illustrated in FIG. 1, and has a plurality of magnetic field generation coil units 11A. Here, the magnetic field generation coil unit is a conductive wire forming a closed loop (or a loop partially non-contiguous) of the smallest unit for generating a magnetic field in one direction by current flow. The coordinates illustrated in FIG. 4A coincide with the coordinates in FIG. 3. That is, the x direction in FIG. 4A coincides with the x direction of power supply coil 30, and the y direction in FIG. 4A coincides with the y direction of power supply coil 30.

In a case an area of a region in which foreign matter 160 has to be detected is small, one magnetic field generation coil is sufficient. On the other hand, in a field of an electric vehicle (EV), since size of the power supply coil is large and foreign matter 160 has to be detected in a wide region, a plurality of the magnetic field generation coil units is required.

As illustrated in FIG. 4A, the plurality of magnetic field generation coil units 11A is arranged in line at equal intervals in the x direction on magnetic field generation coil substrate 110 illustrated in FIG. 1. The shape of each of magnetic field generation coil units 11A has length in the y direction c1 longer than length in the x direction a1 and interval in the x direction b1, and is a vertically long shape. The above vertically long magnetic field generation coil 10A is suitable for a combination with solenoid type power supply coil 30.

In FIG. 4A, currents flowing through magnetic field generation coil units 11A all flow in right-hand (clockwise) direction. Directions of the currents of magnetic field generation coil units 11A are the same as each other, whereby the generated magnetic field can be strengthened.

Width a1 and interval b1 of magnetic field generation coil units 11A are preferably the same. From this, strength of a downward magnetic field and strength of an upward magnetic field are the same as each other. Width a1 and interval b1 may be different from each other.

In the present specification, downward is defined as a direction toward the back of the paper and upward is defined as a direction toward the front of the paper. A direction of current flowing and a magnetic field direction generated by the current can be understood by the right handed-screw rule.

Here, the shape of magnetic field generation coil 10A preferably corresponds to the shape of the sensor coil of sensor coil substrate 140. That is, magnetic field generation coil units 11A preferably correspond to the shape of one sensor coil or a plurality of sensor coils arranged contiguously. For example, when the sensor coil is rectangular, the magnetic field generation coil is preferably rectangular as magnetic field generation coil units 11A of FIG. 4A. When the sensor coil is hexagonal, it is sufficient to match the shape of an outer frame when the sensor coils are lined in the y direction, with the shape of the magnetic field generation coil unit. However, it is necessary to consider a sign of an output voltage of the sensor coil.

Here, when the magnetic field generation coil units are arranged in line, a region formed by the outermost frame of the magnetic field generation coil units is referred to as a magnetic field generation coil array, and when the sensor coils are arranged in line, a region formed by the outermost frame of the sensor coils is referred to as a sensor coil array. At this time, the size of the magnetic field generation coil array is the same level as the size of the sensor coil array, and is required to be the same level as a region in which foreign matter 160 may exist. The magnetic field generation coil array and the sensor coil array are required to be arranged to overlap each other in not only the size but also the position.

Each of magnetic field generation coil units 11A illustrated in FIG. 4A is a magnetic field generation coil of a vertically long shape; however the coil unit may have a horizontally long shape depending on characteristics to be given to the sensor coil. That is, it is necessary to determine the shapes and characteristics of the magnetic field generation coil unit and sensor coil depending on a mutual relationship between characteristics including the shape of the magnetic field generation coil, characteristics including the shape of the sensor coil, a location and characteristics of foreign matter that needs to be sensed, and characteristics of a magnetic field generated by sources other than the magnetic field generation coil.

Figure 4B:
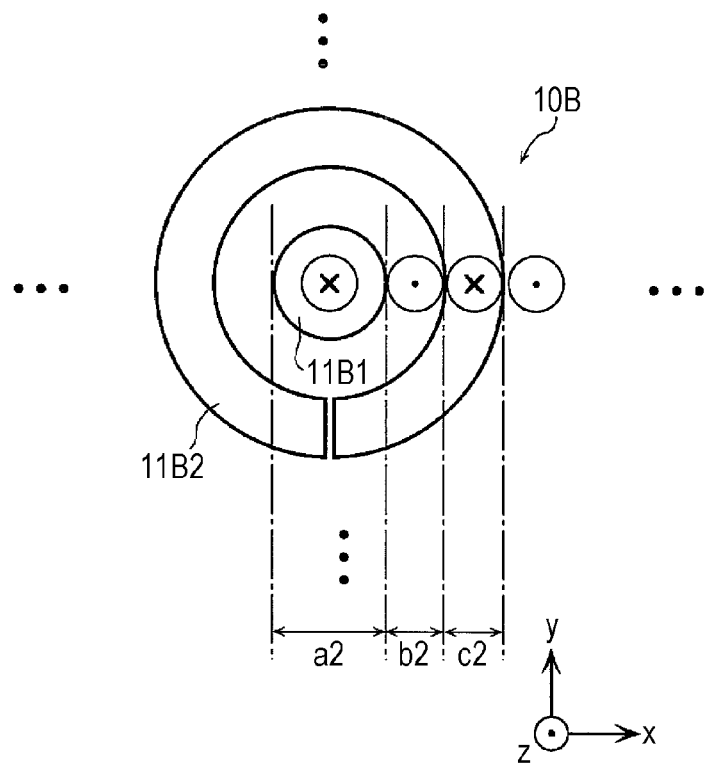
FIG. 4B is a plan view illustrating a shape of a magnetic field generation coil according to a first modification of the exemplary embodiment.

FIG. 4B is a plan view illustrating a shape of a magnetic field generation coil according to a first modification of the exemplary embodiment. Magnetic field generation coil 10B represented in FIG. 4B has magnetic field generation coil units 11B1 and 11B2. Magnetic field generation coil unit 11B1 disposed at the central portion has a circular shape, and magnetic field generation coil unit 11B2 disposed at the outer circumferential portion has a donut shape (circular ring shape). In the present modification, a case is exemplified in which the number of magnetic field generation coil units is two; however, the number of magnetic field generation coil units may be three or more.

In FIG. 4B, a2 is a diameter of magnetic field generation coil unit 11B1, b2 is an interval between magnetic field generation coil units 11B1 and 11B2, and c2 is a width of magnetic field generation coil unit 11B2. Here, a2, b2 and c2 may be the same or different from each other, but preferably correspond to the shape of the sensor coil. From this, foreign matter detection sensitivity is improved. Magnetic field generation coil 10B is suitable for a combination with a spiral type power supply coil. A position of a wiring line configuring a circumference of each magnetic field generation coil unit is preferably caused to coincide with a winding wire position of the spiral type power supply coil. From this, foreign matter detection sensitivity is improved.

An area of the magnetic field generation coil may be configured to be variable.

The direction of the current flowing through the magnetic field generation coil may be fixed, or configured to be variable.

The plurality of the magnetic field generation coil units may be independently driven electrically, may be driven by connecting the plurality of the magnetic field generation coil units together in parallel, or may be driven by connecting the coil units together in series.

The plurality of the magnetic field generation coil units may be formed electrically in series and contiguously (in a layout of one-stroke sketch), as illustrated in modifications 5A to 5C below.

Figure 5A:
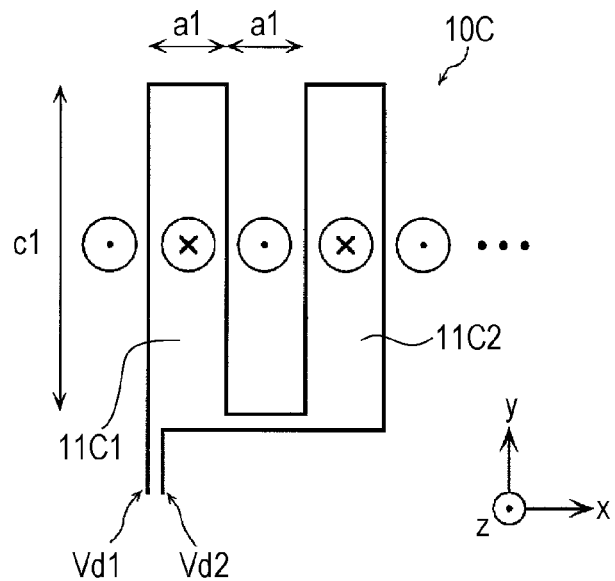
FIG. 5A is a plan view illustrating a shape of a magnetic field generation coil according to a second modification of the exemplary embodiment.

FIG. 5A is a plan view illustrating a shape of a magnetic field generation coil according to a second modification of the exemplary embodiment. Magnetic field generation coil 10C represented in FIG. 5A has magnetic field generation coil units 11C1 and 11C2. Magnetic field generation coil 10C represented in FIG. 5A is an example in which magnetic field generation coil 10A represented in FIG. 4A is formed electrically in series and contiguously (in a method of one-stroke sketch).

Figure 5B:
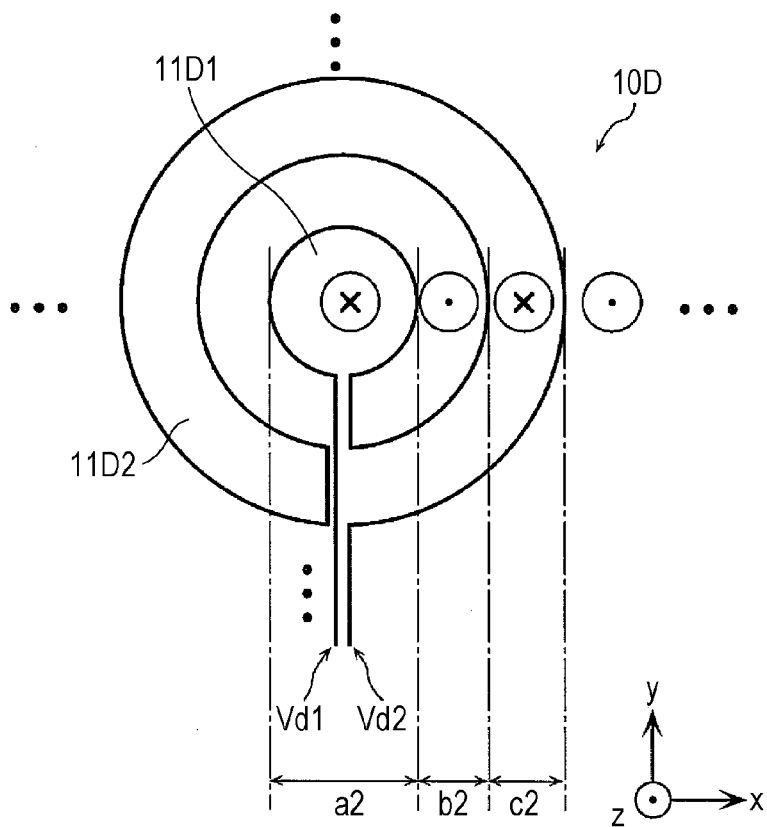
FIG. 5B is a plan view illustrating a shape of a magnetic field generation coil according to a third modification of the exemplary embodiment.

FIG. 5B is a plan view illustrating a shape of a magnetic field generation coil according to a third modification of the exemplary embodiment. Magnetic field generation coil 10D represented in FIG. 5B has magnetic field generation coil units 11D1 and 11D2. Magnetic field generation coil 10D represented in FIG. 5B is an example in which magnetic field generation coil 10B represented in FIG. 4B is formed electrically in series and contiguously (in a method of one-stroke sketch).

Figure 5C:
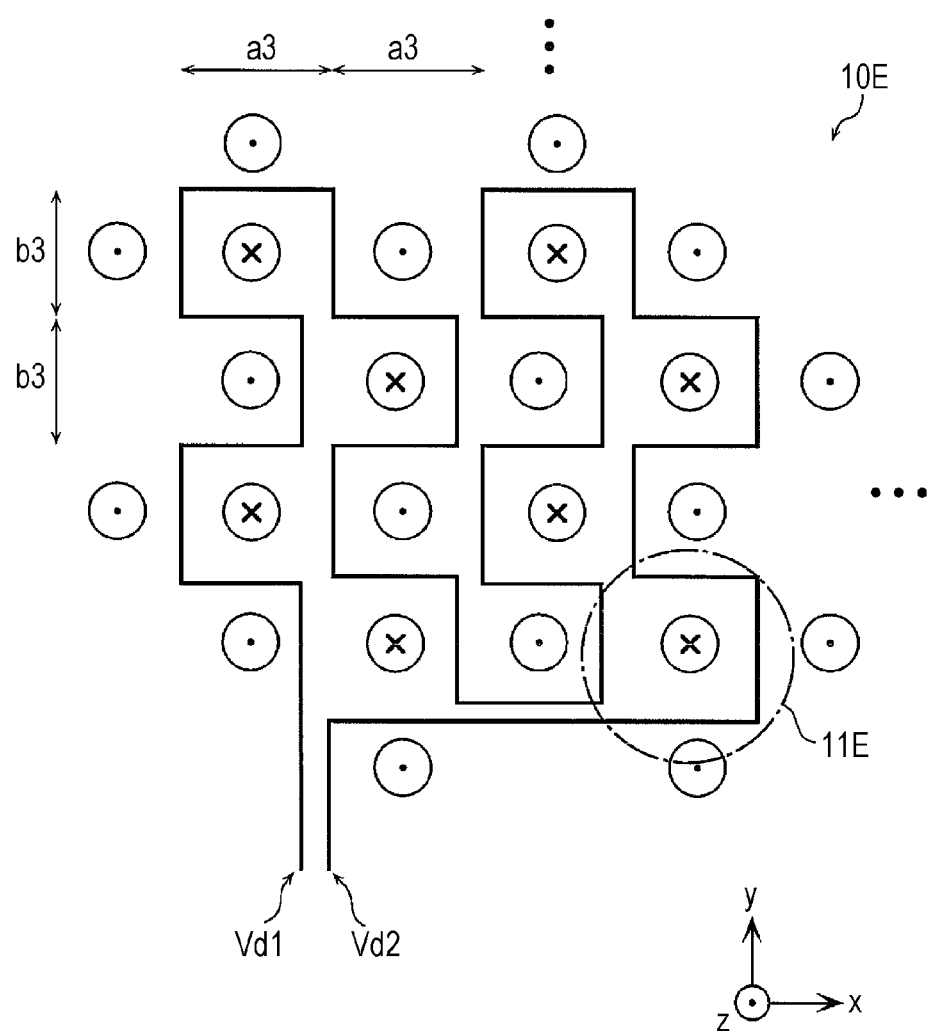
FIG. 5C is a plan view illustrating a shape of a magnetic field generation coil according to a fourth modification of the exemplary embodiment.

FIG. 5C is a plan view illustrating a shape of a magnetic field generation coil according to a fourth modification of the exemplary embodiment. Magnetic field generation coil 10E represented in FIG. 5C has a plurality of magnetic field generation coil units 11E. Magnetic field generation coil 10E represented in FIG. 5C is an example in which a small rectangular magnetic field generation coil units 11E are formed electrically in series and contiguously (in a method of one-stroke sketch).

As illustrated in FIG. 5A to FIG. 5C, the plurality of the magnetic field generation coil units is formed electrically in series and contiguously (in a method of one-stroke sketch), whereby a conductive wiring line forming the magnetic field generation coil can be decreased to a minimum of one. From this, it is not necessary to apply voltage separately to each magnetic field generation coil unit, and terminals can be one set for applying a predetermined potential difference (Vd1-Vd2) to the magnetic field generation coil. Accordingly, simplification can be achieved of the drive circuit for driving the magnetic field generation coil, so that it is possible to achieve reliability improvement, weight and size reduction, and cost reduction by reducing the number of parts.

Here, in the magnetic field generation coil of FIG. 5A to FIG. 5C, directions of the magnetic fields are opposite to each other in regions sectioned by the magnetic field generation coil units.

The shape of the magnetic field generation coil unit formed electrically in series and contiguously (in a method of one-stroke sketch) may be a shape of triangle, rectangle, pentagon, hexagon, circle, donut, or pizza, or may be a shape of a combination thereof.

Magnetic field generation coil 10E illustrated in FIG. 5C is an example of one-stroke sketch in which the plurality of magnetic field generation coil units 11E is arranged also in the y direction, and is suitable for a combination with a solenoid type power supply coil.

The magnetic field generation coil may be formed by subdividing donut-shaped magnetic field generation coil 10D of FIG. 5B with the above one-stroke sketch.

With the magnetic field generation coil layouts illustrated in FIG. 6A to FIG. 7B below, a shape of the magnetic field distribution can be controlled, and various types of foreign matter can be sensed.

Figure 6A:
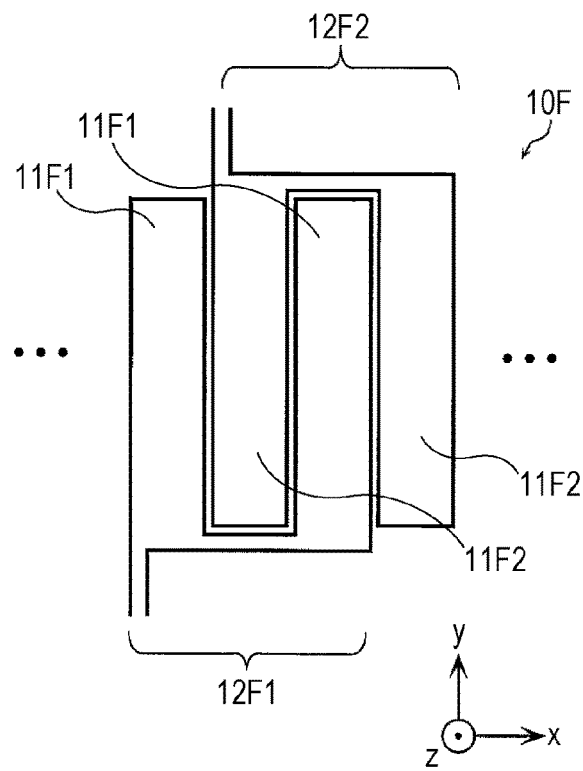
FIG. 6A is a plan view illustrating a shape of a magnetic field generation coil according to a fifth modification of the exemplary embodiment.

FIG. 6A is a plan view illustrating a shape of a magnetic field generation coil according to a fifth modification of the exemplary embodiment. Magnetic field generation coil 10F represented in FIG. 6A has magnetic field generation coil sets 12F1 and 12F2. A magnetic field generation coil set is a unit in which one or more magnetic field generation coil units are formed electrically in series and contiguously (in a method of one-stroke sketch) and that has one set of voltage application terminals. Magnetic field generation coil set 12F1 has a plurality of magnetic field generation coil units 11F1, and magnetic field generation coil set 12F2 has a plurality of magnetic field generation coil units 11F2. From this, each of magnetic field generation coil set 12F1 and magnetic field generation coil set 12F2 has a comb shape formed by the plurality of magnetic field generation coil units. In this way, magnetic field generation coil set 12F1 and magnetic field generation coil set 12F2 each having the comb shape are combined along unevenness of the comb shape.

With the above configuration, magnetic field generation coil 10F is able to adjust arbitrarily a direction of the magnetic field in the outside of magnetic field generation coil unit 11F1 or 11F2.

On the other hand, in a case of magnetic field generation coils 10C and 10E of FIG. 5A and FIG. 5C each configured by one magnetic field generation coil set, a magnetic field direction in a magnetic field generation coil unit and a magnetic field direction in the outside of the magnetic field generation coil unit are always opposite to each other.

In magnetic field generation coil 10F of FIG. 6A, each of the plurality of magnetic field generation coil units 11F1 and the plurality of magnetic field generation coil units 11F2 is connected together in series, but may be connected together in parallel. However, in a case of parallel connection, it is necessary to make resistance of a wiring line for the connection smaller than resistance of a wiring line forming the magnetic field generation coil unit. From this, currents flowing through magnetic field generation coil units are the same level with each other. On the other hand, in a case the resistance of the wiring line for the connection of the magnetic field generation coil unit is not sufficiently small, a current of the magnetic field generation coil unit near the voltage application terminals is large, and a current of the magnetic field generation coil unit far from the voltage application terminals is small. For this reason, a uniform magnetic field cannot be generated in the magnetic field generation coil.

Figure 6B:
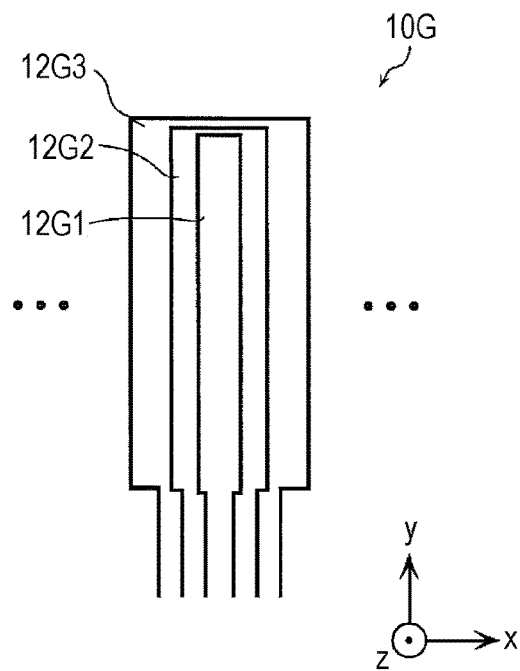
FIG. 6B is a plan view illustrating a shape of a magnetic field generation coil according to a sixth modification of the exemplary embodiment.

FIG. 6B is a plan view illustrating a shape of a magnetic field generation coil according to a sixth modification of the exemplary embodiment. Magnetic field generation coil 10G represented in FIG. 6B has magnetic field generation coil sets 12G1, 12G2, and 12G3. Here, magnetic field generation coil sets 12G1, 12G2, and 12G3 respectively have different areas in the coils. With this configuration, when current directions of the magnetic field generation coil sets are the same as each other, the magnetic field of the central portion can be maximized.

The connection of the magnetic field generation coil sets may be a serial connection, or may be a parallel connection.

Figure 7A:
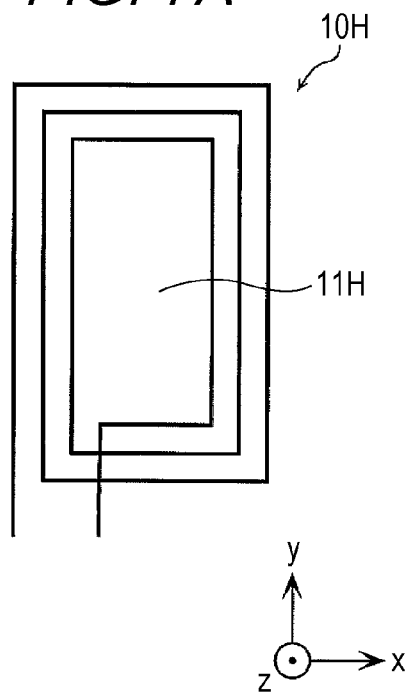
FIG. 7A is a plan view illustrating a shape of a magnetic field generation coil according to a seventh modification of the exemplary embodiment.

FIG. 7A is a plan view illustrating a shape of a magnetic field generation coil according to a seventh modification of the exemplary embodiment. Magnetic field generation coil 10H represented in FIG. 7A has one magnetic field generation coil unit 11H. Here, magnetic field generation coil unit 11H is wound a plurality of times. With this configuration, the magnetic field of the central portion can be maximized.

Figure 7B:
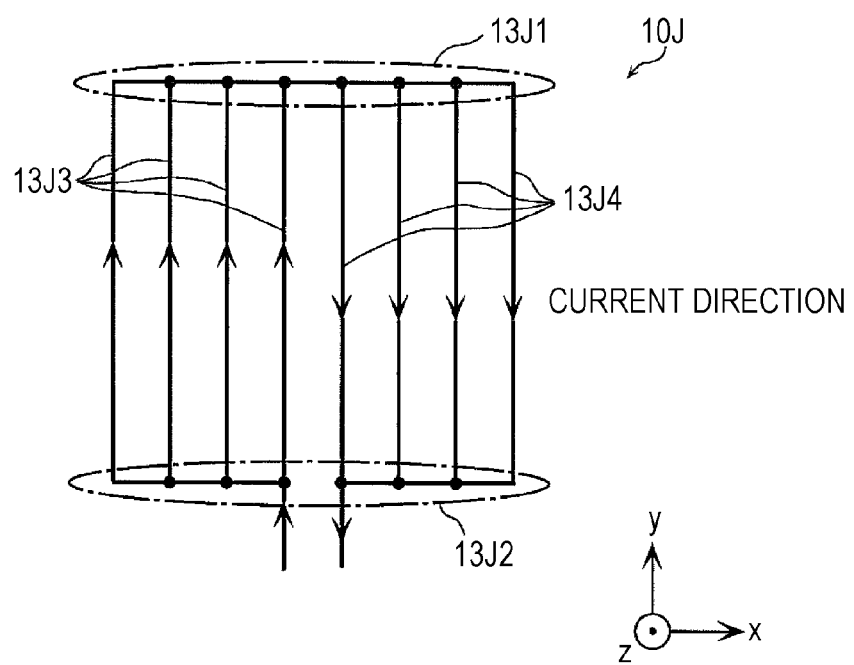
FIG. 7B is a plan view illustrating a shape of a magnetic field generation coil according to an eighth modification of the exemplary embodiment.

FIG. 7B is a plan view illustrating a shape of a magnetic field generation coil according to an eighth modification of the exemplary embodiment. Magnetic field generation coil 10J represented in FIG. 7B has a magnetic field generation coil set configured by parallel wire connections 13J1 and 13J2, four magnetic field generation coil unit lines 13J3, and four magnetic field generation coil unit lines 13J4. In magnetic field generation coil 10J of the above configuration, a magnetic field of a region of the central portion can be maximized by causing a current to flow in the y axis positive direction for each of four magnetic field generation coil unit lines 13J3, and by causing a current to flow in the y axis negative direction for each of four magnetic field generation coil unit lines 13J4, for example. Magnetic field generation coil 10J can be regarded as a modification of magnetic field generation coil 10G in FIG. 6B.

Resistance of each of parallel wire connections 13J1 and 13J2 is required to be smaller than resistance of each of magnetic field generation coil unit lines 13J3 and 13J4. From this, currents flowing through magnetic field generation coil unit lines are the same level with each other. On the other hand, in a case the resistance of each of parallel wire connections 13J1 and 13J2 is not sufficiently small, a current of the magnetic field generation coil unit line near the voltage application terminals is large, and a current of the magnetic field generation coil unit line far from the voltage application terminals is small. For this reason, a uniform magnetic field cannot be generated in the magnetic field generation coil.

In magnetic field generation coils 10A to 10J according to the exemplary embodiment described above, a position of a side forming the magnetic field generation coil unit is preferably disposed to be caused to coincide with a position of a side of the sensor coil unit. Here, the sensor coil unit is a conductive wire forming a closed loop (or a loop partially non-contiguous) of the smallest unit for detecting the magnetic flux change.

On the other hand, in a case the sides do not coincide with each other, an amount of magnetic field as a vector quantity is reduced by lines of magnetic flux toward the opposite direction passing through one sensor coil unit. Therefore, foreign matter detection sensitivity is reduced. From this viewpoint, the sides of the magnetic field generation coil unit and the sensor coil unit are caused to coincide with each other, whereby an amount of magnetic flux passing through the sensor coil unit can be maximized, and foreign matter detection sensitivity can be improved.

One or more sensor coil units are preferably included in the magnetic field generation coil unit.

Size of a magnetic field generation coil unit influences the shape of the magnetic field distribution generated by the coil unit. Foreign matter detection sensitivity is significantly influenced by a location and size of foreign matter 160. Accordingly, a shape and size of the optimal unit magnetic field generation coil are preferably determined according to conditions of foreign matter 160 to be detected and its location. Meanwhile, a shape and size of the sensor coil unit are preferably determined according to foreign matter 160 to be detected and the arrangement location, similarly. From this viewpoint, the shapes and sizes of the magnetic field generation coil unit and the sensor coil unit do not always coincide with each other. A shape and size of one of the magnetic field generation coil unit and the sensor coil unit influence an optimal shape and size of the other. The shapes and sizes of the magnetic field generation coil unit and the sensor coil unit are preferably optimized in this relationship.

Here, when the aforementioned condition is added that the position of the side of the sensor coil unit and the position of the side of the magnetic field generation coil unit are caused to coincide with each other, in a case a width (length of the side) of the sensor coil unit and a width (length of the side) of the magnetic field generation coil unit are different from each other, a plurality of sensor coil units may be disposed in the magnetic field generation coil unit. For example, in a case a distance is long between the magnetic field generation coil and foreign matter, a longer width of the magnetic field generation coil unit is better, and in a case of detecting small foreign matter, a shorter width of the sensor coil unit is better. From this relationship, a width of an integer multiple of the sensor coil unit is a width of the magnetic field generation coil unit.

On the contrary, in a case the distance is short between the magnetic field generation coil and foreign matter, and relatively large foreign matter has to be detected, foreign matter sensing sensitivity is improved as the width of the sensor coil unit is longer than the width of the magnetic field generation coil unit. In this case, it is sufficient that the width is made so that one or several times of magnetic field generation coil units are included in the sensor coil unit, and the sides of the magnetic field generation coil unit and the sensor coil unit are disposed to coincide with each other.

The above relationship between the side forming the sensor coil unit and the side forming the magnetic field generation coil unit is a condition that can be applied in the sensor coil unit of any shape.

In the following, a configuration is described which is capable of selecting a magnetic field generation coil unit through which the current is caused to flow when the plurality of the magnetic field generation coil units exists in the magnetic field generation coil, or a configuration is described which is capable of changing the current direction of the magnetic field generation coil unit.

Figure 8A:
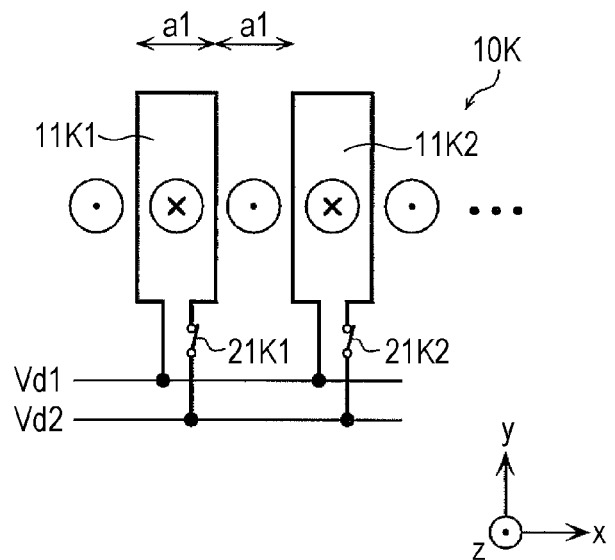
FIG. 8A is a plan view illustrating a shape of a magnetic field generation coil according to a ninth modification of the exemplary embodiment.

FIG. 8A is a plan view illustrating a shape of a magnetic field generation coil according to a ninth modification of the exemplary embodiment. Magnetic field generation coil 10K illustrated in FIG. 8A has a plurality of magnetic field generation coil units 11K1 and 11K2, voltage application terminals for supplying current to the plurality of the magnetic field generation coil units, switch 21K1 provided between magnetic field generation coil unit 11K1 and the voltage application terminal, and switch 21K2 provided between magnetic field generation coil unit 11K2 and the voltage application terminal. Switch 21K1 is a first switch element for selecting whether or not to supply the current to magnetic field generation coil unit 11K1. Switch 21K2 is a first switch element for selecting whether or not to supply the current to magnetic field generation coil unit 11K2.

In FIG. 8A, a configuration is represented in which the plurality of rectangular magnetic field generation coil units 11K1 and 11K2 are respectively connected to switches 21K1 and 21K2, and a magnetic field generation coil unit to be driven can be selected by on/off of the switches. Vd1 and Vd2 are applied to the voltage application terminals of the magnetic field generation coil unit, respectively. On/off switching of switches 21K1 and 21K2 is executed by the drive circuit, for example. In FIG. 8A, the currents flowing through the magnetic field generation coil unit selected flow in the same direction, but may flow in different directions. An interval of wiring lines to which Vd1 and Vd2 are applied is arbitrary; however, in a case a magnetic field created by the wiring lines adversely affects the other devices, the interval of the wiring lines is preferably as short as possible. The other devices mentioned herein include a sensor coil, a power transmission coil, an electrical circuit, and an electronic circuit.

Figure 8B:
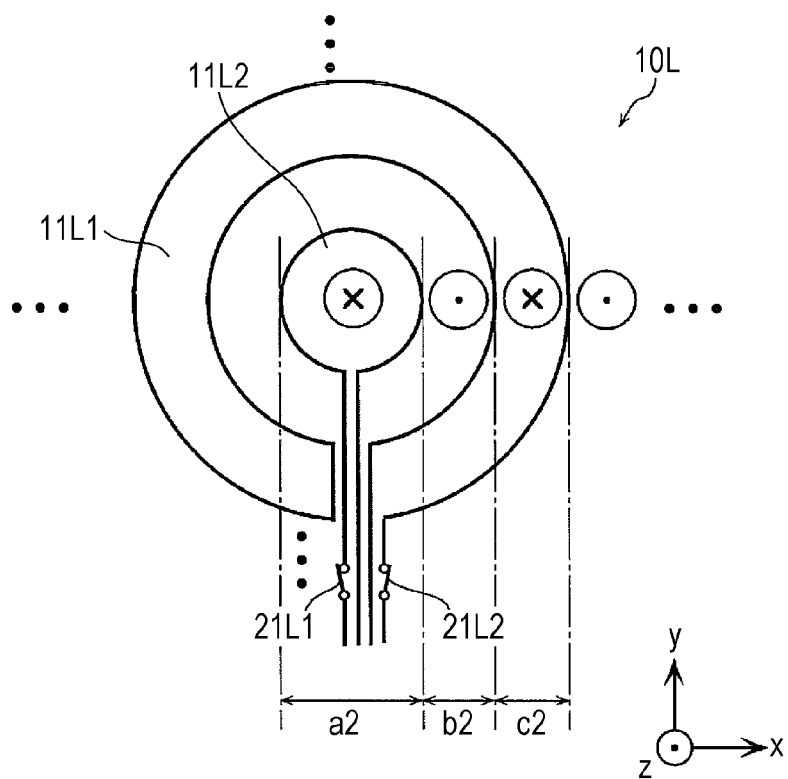
FIG. 8B is a plan view illustrating a shape of a magnetic field generation coil according to a tenth modification of the exemplary embodiment.

FIG. 8B is a plan view illustrating a shape of a magnetic field generation coil according to a tenth modification of the exemplary embodiment. Magnetic field generation coil 10L illustrated in FIG. 8B is an example in which the concept of magnetic field generation coil 10K illustrated in FIG. 8A is embodied in circular and donut-shaped magnetic field generation coil units. In magnetic field generation coil 10L, circular magnetic field generation coil unit 11L1 and donut-shaped magnetic field generation coil unit 11L2 are respectively connected to switches 21L2 and 21L1. On/off switching of switches 21L1 and 21L2 is executed by the drive circuit, for example.

Figure 9A:
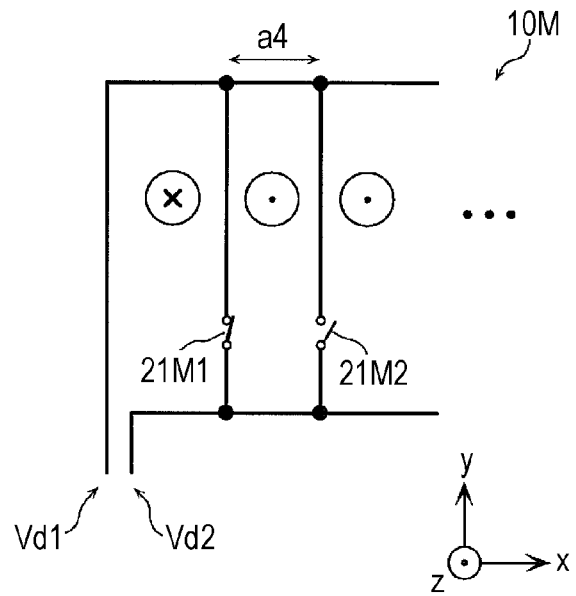
FIG. 9A is a plan view illustrating a shape of a magnetic field generation coil according to an eleventh modification of the exemplary embodiment.

FIG. 9A is a plan view illustrating a shape of a magnetic field generation coil according to an eleventh modification of the exemplary embodiment. Magnetic field generation coil 10M illustrated in FIG. 9A is an example in which the number of magnetic field generation coil units to be selected and an area of the magnetic field generation coil unit to be selected are variable. Specifically, switches 21M1 and 21M2 are disposed on a plurality of coil unit wiring lines. By turning on/off switches 21M1 and 21M2, the current of the coil unit wiring lines configuring the magnetic field generation coil unit can be controlled. Magnetic field directions illustrated in FIG. 9A are examples in a case Vd1>Vd2, switch 21M1 is turned on, and switch 21M2 is turned off.

Figure 9B:
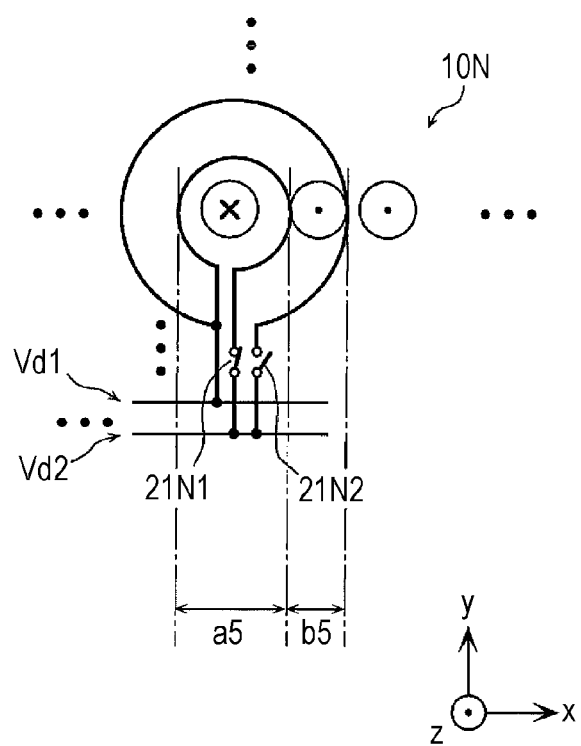
FIG. 9B is a plan view illustrating a shape of a magnetic field generation coil according to a twelfth modification of the exemplary embodiment.

FIG. 9B is a plan view illustrating a shape of a magnetic field generation coil according to a twelfth modification of the exemplary embodiment. Magnetic field generation coil 10N illustrated in FIG. 9B is an example in which the concept of magnetic field generation coil 10M illustrated in FIG. 9A is embodied in circular and donut-shaped magnetic field generation coil units. Specifically, switches 21N1 and 21N2 are disposed on a plurality of coil unit wiring lines. By turning on/off switches 21N1 and 21N2, the current of the coil unit wiring line configuring the magnetic field generation coil unit can be controlled. Magnetic field directions illustrated in FIG. 9B are examples in a case Vd1>Vd2, switch 21N1 is turned on, and switch 21N2 is turned off.

In the configurations of FIG. 8A to FIG. 9B, by switching on/off of the switches, it is possible to change the magnetic field direction of the magnetic field generation coil, magnitude of the magnetic field, the number of magnetic field generation coil units, and their location dependence. As a result, the distribution of the magnetic field created by the magnetic field generation coil can be changed. From this, it is possible to improve foreign matter detection sensitivity that depends on foreign matter having various characteristics and sizes, and a location in which foreign matter exists. The location in which foreign matter exists is a location in a three-dimensional space including the x, y, and z directions.

Further, by a relationship between magnitudes of voltages of Vd1 and Vd2, the direction and magnitude of the current of the magnetic field generation coil can be changed.

Figure 10A:
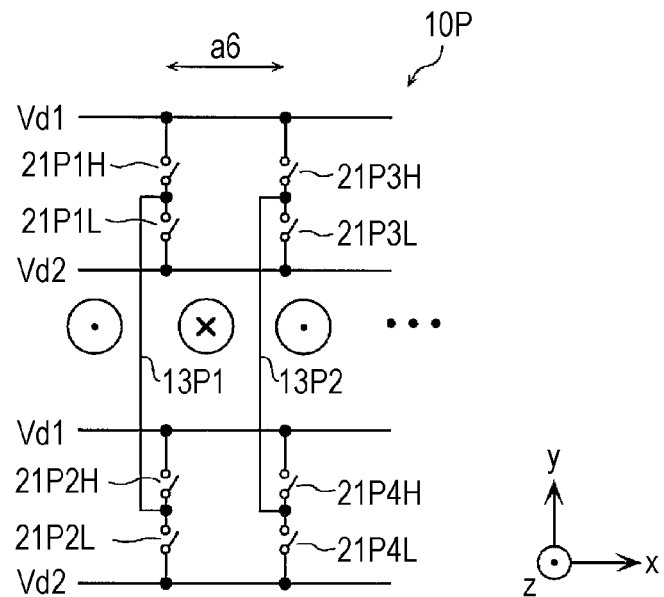
FIG. 10A is a plan view illustrating a shape of a magnetic field generation coil according to a thirteenth modification of the exemplary embodiment.

FIG. 10A is a plan view illustrating a shape of a magnetic field generation coil according to a thirteenth modification of the exemplary embodiment. Magnetic field generation coil 10P illustrated in FIG. 10A has magnetic field generation coil unit lines 13P1 and 13P2, voltage application terminals for supplying current to magnetic field generation coil unit lines 13P1 and 13P2, and switches 21P1H, 21P1L, 21P2H, 21P2L, 21P3H, 21P3L, 21P4H, and 21P4L. Switches 21P1H, 21P1L, 21P2H, 21P2L, 21P3H, 21P3L, 21P4H, and 21P4L are provided between the magnetic field generation coil unit lines and the voltage application terminals, and are second switch elements for changing the direction of the current flowing through the magnetic field generation coil unit lines 13P1 and 13P2.

Magnetic field generation coil unit lines 13P1 and 13P2 are lines configuring the coil units. One end of magnetic field generation coil unit line 13P1 is connected to a power line for applying Vd1 through switch 21P1H, and is connected to a power line for applying Vd2 through switch 21P1L. The other end of magnetic field generation coil unit line 13P1 is connected to the power line for applying Vd1 through switch 21P2H, and is connected to the power line for applying Vd2 through switch 21P2L. One end of magnetic field generation coil unit line 13P2 is connected to a power line for applying Vd1 through switch 21P3H, and is connected to a power line for applying Vd2 through switch 21P3L. The other end of magnetic field generation coil unit line 13P2 is connected to the power line for applying Vd1 through switch 21P4H, and is connected to the power line for applying Vd2 through switch 21P4L.

Magnetic field generation coil 10P is a configuration example in which Vd1 or Vd2 can be selectively applied to each of the voltage application terminals, or no voltage can be applied and the terminals can be caused to be opened, by providing two switches respectively to the two voltage application terminals of the magnetic field generation coil unit line.

Application of Vd1 and Vd2 to the magnetic field generation coil unit line is executed by the drive circuit for driving the magnetic field generation coil. Vd1 and Vd2 are different voltages, and their potential difference is applied to the magnetic field generation coil.

In the above configuration, Vd1 or Vd2 is applied to each end of the magnetic field generation coil unit lines 13P1 and 13P2, whereby one or more magnetic field generation coil units can be formed.

In a case magnetic field generation coil 10P is caused to generate the magnetic field, the drive circuit turns on/off each switch such that the current flows through the magnetic field generation coil unit line. For example, Vd2 is applied to one end (upper side in the figure) of magnetic field generation coil unit line 13P1 by turning off switch 21P1H and turning on switch 21P1L. Meanwhile, Vd1 is applied to the other end (lower side in the figure) of magnetic field generation coil unit line 13P1 by turning on switch 21P2H and turning off switch 21P2L. Here, in a case Vd1>Vd2, the current flowing through magnetic field generation coil unit line 13P1 is directed upward (y axis positive direction). Vd1 is applied to one end (upper side in the figure) of magnetic field generation coil unit line 13P2 by turning on switch 21P3H and turning off switch 21P3L. Meanwhile, Vd2 is applied to the other end (lower side in the figure) of magnetic field generation coil unit line 13P2 by turning off switch 21P4H and turning on switch 21P4L. Here, in a case Vd1>Vd2, the current flowing through magnetic field generation coil unit line 13P2 is directed downward (y axis negative direction).

Due to flow of the currents of magnetic field generation coil unit lines 13P1 and 13P2 described above, the magnetic field direction is directed downward (z axis negative direction) in a region sandwiched between magnetic field generation coil unit lines 13P1 and 13P2. In this way, currents are caused to flow in opposite directions to each other respectively through adjacent two magnetic field generation coil unit lines, whereby strength of the magnetic field in the region sandwiched between the two magnetic field generation coil unit lines can be increased.

By inverting on/off states of switches 21P1H, 21P1L, 21P2H, 21P2L, 21P3H, 21P3L, 21P4H, and 21P4L from the above states, the current flowing through magnetic field generation coil unit line 13P1 is directed downward (y axis negative direction). The current flowing through magnetic field generation coil unit line 13P2 is directed upward (y axis positive direction). Due to such flow of the currents of magnetic field generation coil unit lines 13P1 and 13P2, the magnetic field direction is directed upward (z axis positive direction) in a region sandwiched between magnetic field generation coil unit lines 13P1 and 13P2.

With the configuration of magnetic field generation coil 10P, the magnetic field direction can be inverted by controlling on/off of the above switches.

To avoid short circuit of the output of the drive circuit, switch 21P1H and switch 21P1L are not turned on at the same time. Switch 21P2H and switch 21P2L are not turned on at the same time. Switch 21P3H and switch 21P3L are not turned on at the same time. Switch 21P4H and switch 21P4L are not turned on at the same time.

For example, switch 21P1H and switch 21P1L may be turned off at the same time. From this, one end (upper side in the figure) of magnetic field generation coil unit line 13P1 is opened. For example, switch 21P2H and switch 21P2L may be turned off at the same time. From this, the other end (lower side in the figure) of magnetic field generation coil unit line 13P1 is opened. In this way, the current can be prevented from flowing through magnetic field generation coil unit line 13P1 by causing one end or the other end, or both ends of magnetic field generation coil unit line 13P1 to be opened.

The switch may be semiconductor electronic devices, relays, or mechanical switches. Switches of the semiconductor electronic devices include a metal-oxide-semiconductor field-effect transistor (MOSFET), an insulated gate bipolar transistor (IGBT), and a bipolar junction transistor (BJT). Materials of the above semiconductor electronic devices include Si, SiC, and GaN. The switches according to the present modification are preferably the ones each of which has high breakdown voltage and low on-resistance for reducing loss. From this viewpoint, the IGBT or the BJT is desirable, and the one using SiC material is desirable.

The drive circuit may control on/off of the switches connected to magnetic field generation coil unit line 13P1 and 13P2 independently, or such that on/off of the switches are in association with each other.

Magnetic field generation coil 10P is an example in which the rectangular magnetic field generation coil unit is modified, and is suitable for a combination with a solenoid type power supply coil.

Figure 10B:
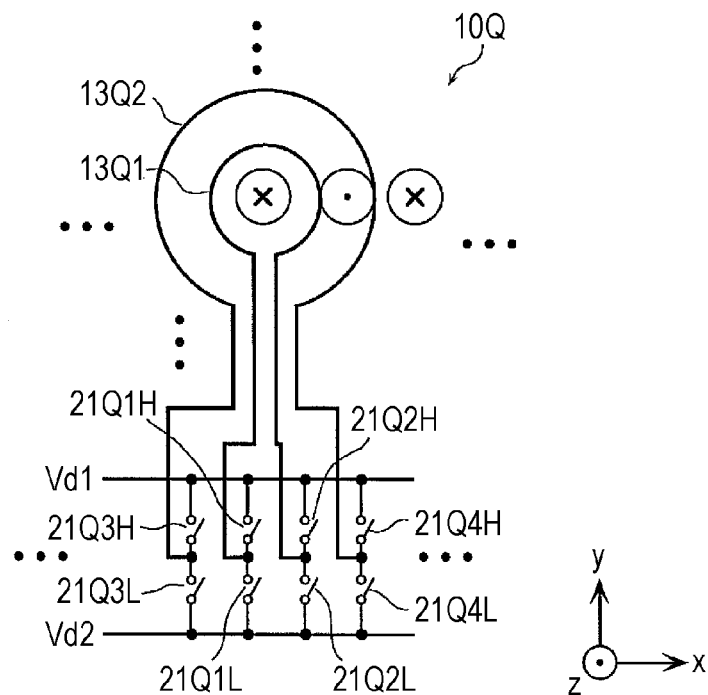
FIG. 10B is a plan view illustrating a shape of a magnetic field generation coil according to a fourteenth modification of the exemplary embodiment.

FIG. 10B is a plan view illustrating a shape of a magnetic field generation coil according to a fourteenth modification of the exemplary embodiment. Magnetic field generation coil 10Q illustrated in FIG. 10B has circular magnetic field generation coil unit lines 13Q1 and 13Q2, switches 21Q1H, 21Q1L, 21Q2H, 21Q2L, 21Q3H, 21Q3L, 21Q4H, and 21Q4L. Magnetic field generation coil 10Q is an example in which magnetic field generation coil 10P is modified to circular and donut-shaped magnetic field generation coils. Hereinafter, regarding magnetic field generation coil 10Q, description of the same points as the configuration of magnetic field generation coil 10P is omitted, and different points are mainly described.

Magnetic field generation coil unit lines 13Q1 and 13Q2 are lines configuring the coil units. One end of magnetic field generation coil unit line 13Q1 is connected to a power line for applying Vd1 through switch 21Q1H, and is connected to a power line for applying Vd2 through switch 21Q1L. The other end of magnetic field generation coil unit line 13Q1 is connected to the power line for applying Vd1 through switch 21Q2H, and is connected to the power line for applying Vd2 through switch 21Q2L. One end of magnetic field generation coil unit line 13Q2 is connected to the power line for applying Vd1 through switch 21Q3H, and is connected to the power line for applying Vd2 through switch 21Q3L. The other end of magnetic field generation coil unit line 13Q2 is connected to the power line for applying Vd1 through switch 21Q4H, and is connected to the power line for applying Vd2 through switch 21Q4L.

Magnetic field generation coil 10Q is a configuration example in which Vd1 or Vd2 can be selectively applied to each of the voltage application terminals, or, no voltage can be applied and the terminals can be caused to be opened by providing two switches respectively to the two voltage application terminals of the magnetic field generation coil unit line.

Application of Vd1 and Vd2 to the magnetic field generation coil unit line is executed by the drive circuit for driving the magnetic field generation coil. Vd1 and Vd2 are different voltages, and their potential difference is applied to the magnetic field generation coil.

In the above configuration, Vd1 or Vd2 is applied to each end of the magnetic field generation coil unit lines 13P1 and 13P2, whereby one or more magnetic field generation coil units can be formed.

In the present modification, the switches are respectively connected to both ends of each of circular magnetic field generation coil unit lines 13Q1 and 13Q2; however, modification may have a configuration in which the magnetic field generation coil unit line is divided into two semicircles, and the switches are respectively connected to both ends of the divided semicircular magnetic field generation coil unit line. Division of the circular magnetic field generation coil unit line may be three or more.

Magnetic field generation coil 10Q is an example in which circular and donut-shaped magnetic field generation coil units are modified, and is suitable for a combination with a spiral type power supply coil.

Here, as is the case of magnetic field generation coils 10P and 10Q, a method of selecting magnetic field generation coil unit line is referred to as a magnetic field generation coil unit line selection method.

Power consumption of the drive circuit for driving the magnetic field generation coil depends on output current, and loss increases as the output current increases. On the other hand, when the current flowing through the magnetic field generation coil is increased, the magnetic field to be generated can be increased, so that foreign matter detection sensitivity is improved.

In particular, in a case of EV application, since high strength is required for a housing of a power supply system disposed on the ground, the thickness of the housing is about 1 cm. When it is considered that foreign matter exists on the housing, the distance from the sensor coil to the foreign matter is about 1 cm. As the distance is increased, sensing sensitivity is reduced since the magnetic field is reduced in the location of the foreign matter. Therefore, to sense the foreign matter with high accuracy, a larger magnetic field is required. Since the power of the power transmission coil in the EV application is large and therefore the current is also large, the magnetic field to be generated by the power transmission coil is increased. Since heat generation of the foreign matter is determined depending on the magnetic field of the power transmission coil, the heat generation of the foreign matter is increased. From this viewpoint, in the EV application field, it is necessary to detect smaller foreign matter, and it is necessary to detect the foreign matter in a farther location.

As described above, in the EV application field, it is necessary to cause a large current to flow through the magnetic field generation coil to improve foreign matter detection sensitivity; however, there is a trade-off relationship between foreign matter detection sensitivity and loss, small size and light weight, and electromagnetic radiation. When a large current is caused to flow, heat generation occurs due to ohmic loss of the magnetic field generation coil itself, and there is a trade-off relationship also between foreign matter detection sensitivity and heat generation. When the cross-sectional area or the surface area of the wiring line forming the coil is increased to reduce ohmic loss of the magnetic field generation coil, heat generation of the wiring line occurs due to the magnetic field generated by the power transmission coil, and there is a trade-off relationship also between the cross-sectional area or the surface area of the coil wiring line and wiring line heat generation.

To improve these trade-offs, the above thirteenth and fourteenth modifications are made to be able to select the magnetic field generation coil unit line configuring the magnetic field generation coil unit.

To drive all of the unit magnetic field generation coils at the same time, a large current is required, so that loss is increased. When the magnetic field generation coil units are connected together in series, a large voltage is required even at the same current, loss is increased, and the magnetic field generation coil unit is required to have a high breakdown voltage at the same time.

Although the location of the foreign matter to be detected is a wide range, driving all magnetic field generation coils at the same time to cover the range causes a loss increase and an increase of heat generation of the magnetic field generation coil.

On the other hand, with the above magnetic field generation coil unit line selection method, foreign matter detection is possible by performing a plurality of times of execution of one foreign matter detection operation with narrow range magnetic field generation and movement in location. From this, it is possible to perform foreign matter detection with high accuracy without increasing loss, and without decreasing detection sensitivity.

Aforementioned magnetic field generation coil 10M of FIG. 9A and magnetic field generation coil 10N of FIG. 9B have some of the characteristics of the magnetic field generation coil unit line selection method. However, in a case the potential difference between Vd1 and Vd2 is constant, the direction of the current of the coil unit wiring line is fixed, and the current direction cannot be changed in magnetic field generation coils 10M and 10N as is the case of magnetic field generation coils 10P and 10Q.

For each of magnetic field generation coils 10P and 10Q, a configuration has been exemplified in which there are two magnetic field generation coil unit lines; however, not limited thereto, there may be three or more magnetic field generation coil unit lines depending on the magnetic field generation range required.

In a case heat generation of the magnetic field generation coil unit line due to ohmic loss is large and the allowable temperature is exceeded when the current is caused to flow through the magnetic field generation coil unit line, a plurality of the magnetic field generation coil unit lines may be arranged to be adjacent to each other and connected together in parallel. From this, the current flowing through one magnetic field generation coil unit line can be reduced, and heat generation temperature can be reduced. Further, the generated magnetic field can be increased when the plurality of the magnetic field generation coil unit lines is arranged to be adjacent to each other, and as a result, foreign matter detection sensitivity is improved.

Figure 10C:
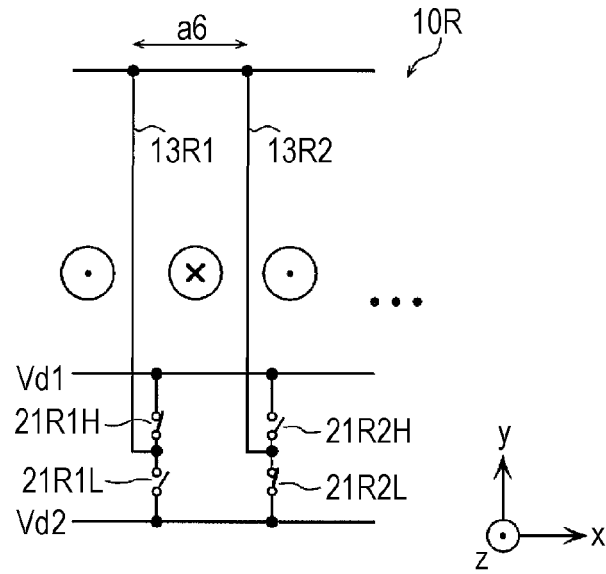
FIG. 10C is a plan view illustrating a shape of a magnetic field generation coil according to a fifteenth modification of the exemplary embodiment.

FIG. 10C is a plan view illustrating a shape of a magnetic field generation coil according to a fifteenth modification of the exemplary embodiment. Magnetic field generation coil 10R illustrated in FIG. 10C is an example in which the magnetic field generation coil 10P is modified such that upper side (y axis positive direction) switches are eliminated.

Magnetic field generation coil 10R has magnetic field generation coil unit lines 13R1 and 13R2, and switches 21R1H, 21R1L, 21R2H, and 21R2L.

Magnetic field generation coil unit lines 13R1 and 13R2 are lines configuring the coil units. One end of magnetic field generation coil unit line 13R1 and one end of magnetic field generation coil unit line 13R2 are connected together through a common wiring line. The other end of magnetic field generation coil unit line 13R1 is connected to the power line for applying Vd1 through switch 21R1H, and is connected to the power line for applying Vd2 through switch 21R1L. The other end of magnetic field generation coil unit line 13R2 is connected to the power line for applying Vd1 through switch 21R2H, and is connected to the power line for applying Vd2 through switch 21R2L.

Magnetic field generation coil 10P is capable of flowing currents through all magnetic field generation coil unit lines selected in the same direction; however, magnetic field generation coil 10R is set such that both directions of the current exist in the magnetic field generation coil unit lines selected. In magnetic field generation coil 10R, the number of magnetic field generation coil unit lines selected has to be two or more.

The number of switches of magnetic field generation coil 10R may be a half of that of magnetic field generation coil 10P, so that cost reduction and downsizing are possible.

Figure 10D:
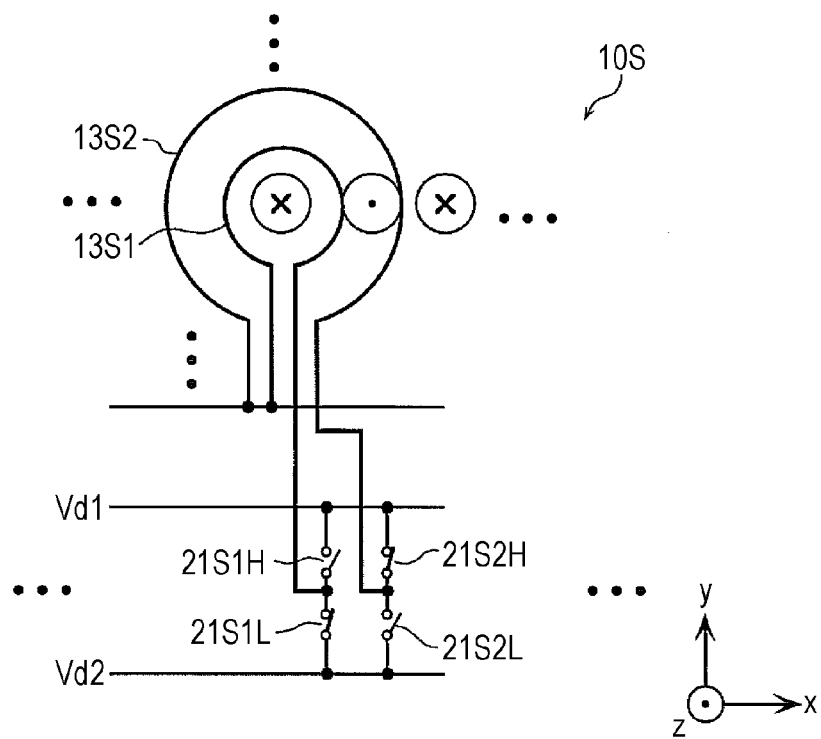
FIG. 10D is a plan view illustrating a shape of a magnetic field generation coil according to a sixteenth modification of the exemplary embodiment.

FIG. 10D is a plan view illustrating a shape of a magnetic field generation coil according to a sixteenth modification of the exemplary embodiment. Magnetic field generation coil 10S illustrated in FIG. 10D is an example in which magnetic field generation coil 10S is modified such that left side (x axis negative direction) switches are eliminated.

Magnetic field generation coil 10S has circular magnetic field generation coil unit lines 13S1 and 13S2, and switches 21S1H, 21S1L, 21S2H, and 21S2L.

Magnetic field generation coil unit lines 13S1 and 13S2 are lines configuring the coil units. One end of magnetic field generation coil unit line 13S1 and one end of magnetic field generation coil unit line 13S2 are connected together through a common wiring line. The other end of magnetic field generation coil unit line 13S1 is connected to the power line for applying Vd1 through switch 21S1H, and is connected to the power line for applying Vd2 through switch 21S1L. The other end of magnetic field generation coil unit line 13S2 is connected to the power line for applying Vd1 through switch 21S2H, and is connected to the power line for applying Vd2 through switch 21S2L.

Magnetic field generation coil 10Q is capable of flowing currents through all magnetic field generation coil unit lines selected in the same direction; however, magnetic field generation coil 10S is set such that both directions of the current exist in the magnetic field generation coil unit lines selected. In magnetic field generation coil 10S, the number of magnetic field generation coil unit lines selected has to be two or more.

The number of switches of magnetic field generation coil 10S may be a half of that of magnetic field generation coil 10Q, so that cost reduction and downsizing are possible.

[3. Optimal Shape of Magnetic Field Generation Coil]

Figure 11A:
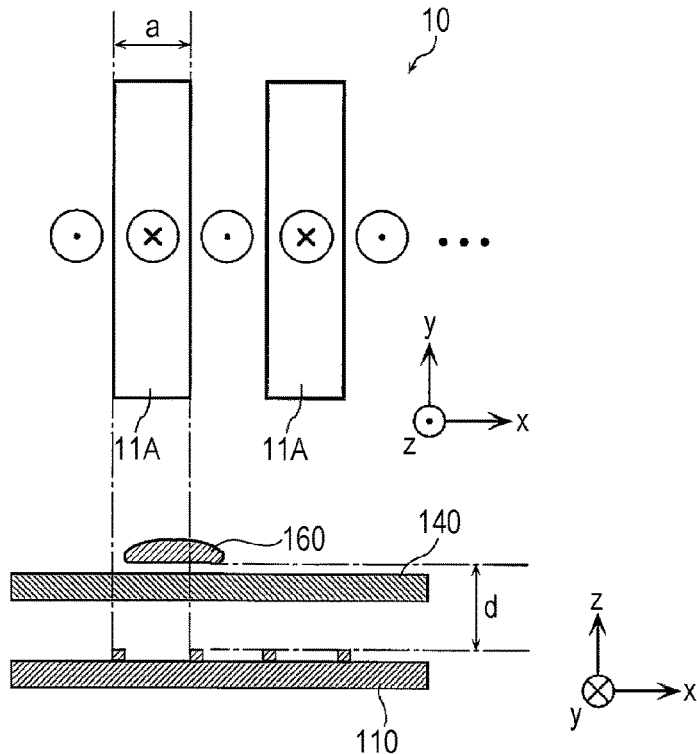
FIG. 11A is a diagram representing a positional relationship between the magnetic field generation coil and foreign matter.
Figure 11B:
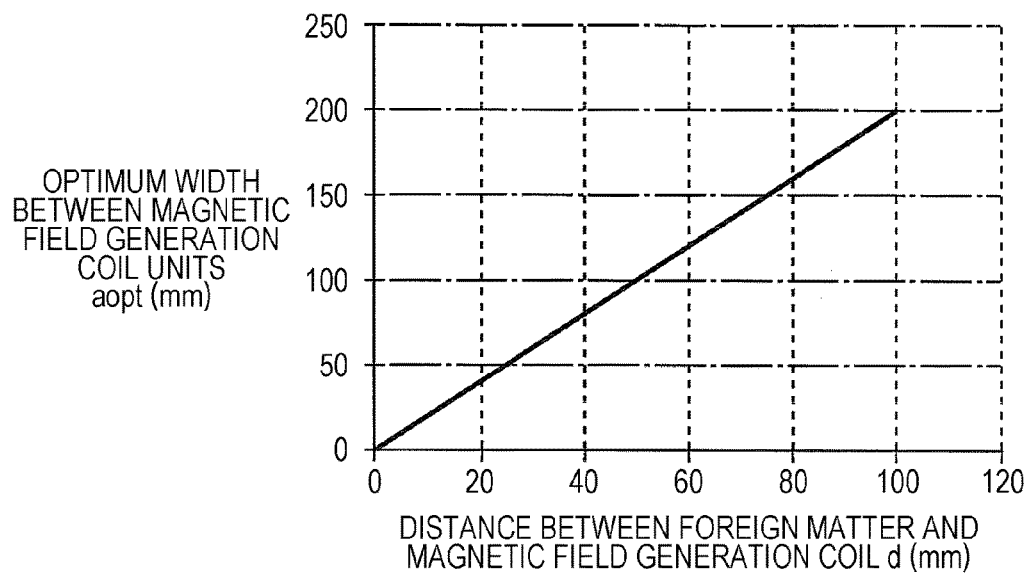
FIG. 11B is a graph representing a relationship between a width of a magnetic field generation coil unit and a distance between the magnetic field generation coil and foreign matter.

FIG. 11A is a diagram representing a positional relationship between the magnetic field generation coil and foreign matter, and FIG. 11B is a graph representing a relationship between a width of the magnetic field generation coil unit and a distance between the magnetic field generation coil and foreign matter. FIG. 11A illustrates an arrangement relationship between magnetic field generation coil substrate 110 on which typical magnetic field generation coil 10 is mounted and sensor coil substrate 140 on which foreign matter 160 exists. Here, d is a distance between magnetic field generation coil substrate 110 and foreign matter 160. Here, it is assumed that foreign matter 160 is attached on a surface of a housing for covering sensor coil substrate 140. In addition, a is a width in the x direction of magnetic field generation coil units 11A configuring magnetic field generation coil 10.

FIG. 11B illustrates a relationship between the distance d and the width a of the optimal magnetic field generation coil unit. A magnitude of the z direction magnetic field generated by magnetic field generation coil 10 is decreased with an increase of the distance in the z direction from magnetic field generation coil 10. The magnetic field in the z direction depends on the width a of the magnetic field generation coil unit, and an optimum width aopt exists in which the z direction magnetic field is maximized when the width a is changed in a certain distance d.

Here, a relationship between the distance d and the optimum width aopt is aopt=(2.0±0.5)×d.

Here, the inventor of the present disclosure has found that foreign matter detection sensitivity is drastically reduced in a case the optimum width aopt is smaller than 1.5×d or greater than 2.5×d. From this, a design value of the width a of the magnetic field generation coil unit is preferably (2.0±0.5)×d.

That is, the width of the magnetic field generation coil unit that is a length of a short side of a rectangle or a width of a circular ring is preferably 1.5 times or more and 2.5 times or less of a distance between foreign matter and a plane including the magnetic field generation coil unit.

[4. Drive Circuit of Magnetic Field Generation Coil]

Foreign matter detection device 1 according to the present exemplary embodiment has a drive circuit for driving the magnetic field generation coil. The drive circuit applies voltages (Vd1 and Vd2) and current to the magnetic field generation coil. Wave forms of the current and voltage to be applied by the drive circuit are sine wave, triangular wave, rectangular wave, pulse wave, and the like.

Foreign matter detection sensitivity is improved as electromotive force of the sensor coil unit is increased. An electromotive force V of the sensor coil unit is proportional to a time change of magnetic flux Φ passing through the inside of the sensor coil unit. Accordingly, foreign matter detection sensitivity is improved as an absolute value of a time change amount of the magnetic flux Φ is increased. Therefore, foreign matter detection sensitivity is improved when the absolute value of a time change amount of the current flowing through the magnetic field generation coil is increased. That is, foreign matter detection sensitivity is improved by increasing, using the drive circuit, the absolute value of the time change amount of the current to be supplied to the magnetic field generation coil.

From this viewpoint, in a case the current waveform is, for example, a sine wave or a triangular wave, the absolute value of the time change amount of the current can be increased by increasing the frequency and the current peak. In a case the current waveform is, for example, a rectangular wave or a pulse wave, the absolute value of the time change amount of the current can be increased by increasing the speed of the rising current and the falling current, and the current peak. That is, the drive circuit preferably drives the magnetic field generation coil by changing at least one of the temporal change amount and the absolute value of at least one of the current, voltage, power, and frequency to be supplied to the magnetic field generation coil unit.

The drive circuit preferably drives the magnetic field generation coil such that a time differential value of the current flowing through the magnetic field generation coil unit is 1 A/50 ns or more. From this, foreign matter detection sensitivity of foreign matter 160 that is a heating element of 80° C. or more is improved.

In the foreign matter detection device according to FIG. 2 and a second exemplary embodiment described later, electromotive force generated by magneto coil 20 drives the magnetic field generation coil. That is, the drive circuit may include magneto coil 20. The electromotive force generated by magneto coil 20 may be used as the power source of the drive circuit. From this, the power source circuit of the drive circuit can be reduced.

[5. Configuration of Magnetic Field Generation Coil Substrate Having Magneto Coil]

In the following, the foreign matter detection device is described to which a magneto coil is added for supplying voltage and current to the magnetic field generation coil.

Figure 12:
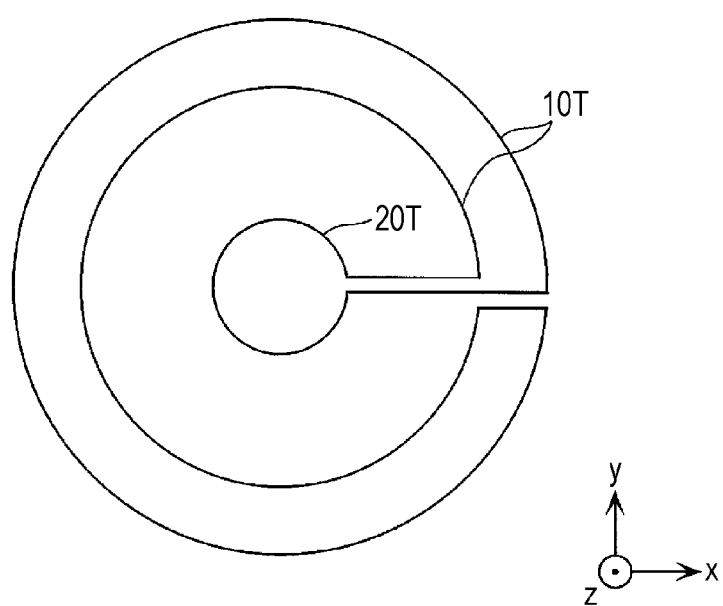
FIG. 12 is a plan view illustrating shapes of a magnetic field generation coil and a magneto coil according to a seventeenth modification of the exemplary embodiment.

FIG. 12 is a plan view illustrating shapes of a magnetic field generation coil and a magneto coil according to a seventeenth modification of the exemplary embodiment. FIG. 12 illustrates donut-shaped magnetic field generation coil 10T and circular magneto coil 20T of when the power transmission coil is a spiral type coil. Magnetic field generation coil 10T and magneto coil 20T are mounted on magnetic field generation coil substrate 110, for example. That is, magnetic field generation coil substrate 110 further has magneto coil 20T for generating electromotive force by using a magnetic field generated by the power supply coil and the power reception coil, and for supplying the electromotive force generated to the magnetic field generation coil unit.

Since the magnetic field is large in a central portion of the spiral type power supply coil, magneto coil 20T is disposed at the central portion. Magnetic field generation coil 10T is disposed at the outer circumferential region of the power supply coil in which the z direction magnetic field is small. Magneto coil 20T and magnetic field generation coil 10T are coupled together with a wiring line. Upon implementing the above configuration, as illustrated in FIG. 12, magneto coil 20T and magnetic field generation coil 10T can be configured by one-stroke sketch method in a plane of one layer.

When the magnetic field is changed with a time division method, a switch is preferably provided further. Intermittent operation of the magnetic field generation with the time division method is able to reduce both power consumption and electromagnetic radiation. Timing of the intermittent operation is synchronized with intermittent operation timing of a detection circuit.

Since power generation is caused by electromotive force also in magnetic field generation coil 10T, a generated voltage of magneto coil 20T is required to be larger than a generated voltage of magnetic field generation coil 10T. A current flowing through magneto coil 20T and magnetic field generation coil 10T is determined depending on a combined voltage of generated voltages of magnetic field generation coil 10T and magneto coil 20T and resistance of the wiring line layout.

FIG. 2 illustrates a configuration example of magneto coil 20 and magnetic field generation coil 10 in a case the power transmission coil is a solenoid type power supply coil. FIG. 12 illustrates a configuration example of magneto coil 20T and magnetic field generation coil 10T in a case the power transmission coil is a spiral type power supply coil.

Here, a combined magnetic field is described that is made by combining the magnetic field generated by the power transmission coil and the magnetic field generated by the magnetic field generation coil, in a case the magnetic field generation coil is disposed at a region in which the magnetic field in the z direction generated by the power transmission coil is near zero.

The region in which the magnetic field in the z direction is near zero is the central region in the x direction in a case of the solenoid type power supply coil, and is a region near the middle point of a straight line connecting the coil center and the coil outermost circumference together in a case of the spiral type power supply coil.

In the case of the solenoid type power supply coil, the x coordinate at which the z direction magnetic field is zero is x=xzh0, and the center of the x direction is x=0. That is, xzh0 exists near x=0. As illustrated in the lower part of FIG. 3, the magnetic field in the z direction in a region in which x<xzh0 and the magnetic field in the z direction in a region in which x>xzh0 are directed to opposite directions to each other.

In the case of the spiral type power supply coil, the winding wire is circular, and the x coordinate of the coil center is 0, the direction from the coil center to the right side coil circumference is x>0, and the direction from the coil center to the left side coil circumference is x<0. Since the spiral type power supply coil is circular, the distribution in the x direction of the magnetic field (the lower part of FIG. 14D described later) is bilaterally symmetrical around x=0, ideally. The x coordinate at which the z direction magnetic field is zero is xzh0, similarly to the case of the solenoid coil. Xzh0 exists at one location in a plus region of x, and exists at one location in a minus region of x. The coordinates are respectively +xzh0 and −xzh0. Incidentally, +xzh0 and −xzh0 respectively exist in regions each of which is apart from the coil center by the same distance. Since the spiral type power supply coil is circular, it is meant that the z direction magnetic field is zero in a region drawing a circle with a radius of xzh0 on the xy plane. The magnetic field in a region in which in which −xzh0<x<+xzh0 and the magnetic field in a region in which x<−xzh0 and x>xzh0 are directed to opposite directions to each other.

When power is generated from the magneto coil by the magnetic field of the power transmission coil, a time when the time change of the current flowing through the magneto coil is a peak value is a time when the voltage generated by the magneto coil is a peak value. The time when the voltage of the magneto coil is the peak value is a time when a time change amount of the magnetic field of the power transmission coil is a peak value. At this time, the current of the power transmission coil is almost zero.

When the current does not flow through the power reception coil, that is, when all of the magnetic fields are generated by the power supply coil, a time change amount of the magnetic field of the magnetic field generation coil is a peak value at the time when the current of the power supply coil is zero.

On the other hand, since the magnetic field generation coil is the combined magnetic field of the magnetic fields by the currents of the power supply coil and the power reception coil when the current also flows through the power reception coil, the time when the time change amount of the magnetic field of the magnetic field generation coil is the peak may be shifted a little from the time when the current of the power transmission coil is zero.

When there is one magnetic field generation coil and the coil is disposed to include x=xzh0, in a case of the solenoid type power supply coil, when directions of the z direction magnetic field of the power transmission coil and the z direction magnetic field of the magnetic field generation coil are the same as each other in the region in which x<xzh0, the z direction magnetic fields strengthen each other in the region, so that foreign matter detection sensitivity is improved. However, since the directions of magnetic fields of the power transmission coil and the magnetic field generation coil are opposite to each other in the region in which x>xzh0, the z direction magnetic fields weaken each other. That is, foreign matter detection sensitivity degrades in the region.

A case of the spiral type power supply coil can also be considered similarly. In the region in which −xzh0<x<+xzh0, the magnetic field in the z direction of the power transmission coil and that of the magnetic field generation coil strengthen each other, so that foreign matter detection sensitivity in the region is improved. However, in regions of x other than the above region, since the magnetic fields weaken each other, foreign matter detection sensitivity degrades, on the contrary.

Configurations to solve the above problem include a configuration for performing foreign matter detection by switching directions of the current flowing through the magnetic field generation coil. That is, a configuration in which the z direction magnetic fields strengthen each other in one magnetic field generation coil of two magnetic field generation coils at the time of one current direction, and the z direction magnetic fields strengthen each other in the other magnetic field generation coil at the time of the opposite current direction. From this, high sensitivity foreign matter detection can be performed in both magnetic field generation coils by performing foreign matter detection in each current direction.

Configuration for inverting the current direction of the magnetic field generation coil include a configuration in which switches are provided between the magneto coil and the magnetic field generation coil, and the current direction is inverted by on/off of the switches.

Another configuration to solve the above problem is described below.

Figure 13A:
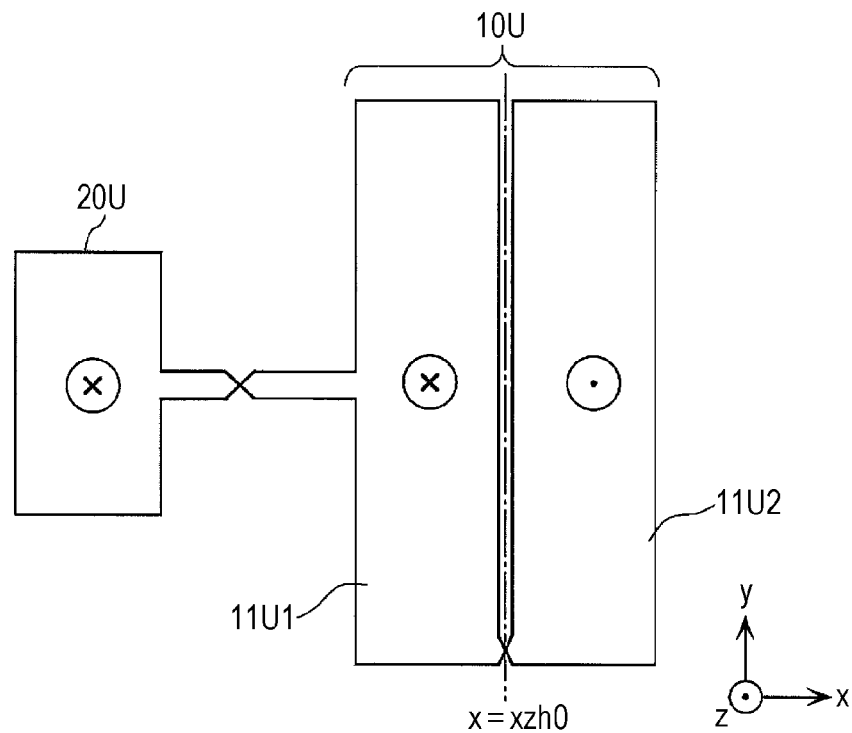
FIG. 13A is a plan view illustrating shapes of a magnetic field generation coil and a magneto coil according to an eighteenth modification of the exemplary embodiment.

FIG. 13A is a plan view illustrating shapes of a magnetic field generation coil and a magneto coil according to an eighteenth modification of the exemplary embodiment. FIG. 13A illustrates a configuration of magnetic field generation coil 10U and magneto coil 20U corresponding to a solenoid type power transmission coil.

Magnetic field generation coil 10U has two magnetic field generation coil units 11U1 and 11U2 in which directions of the respective generated magnetic fields are opposite to each other. When x=xzh0 is a boundary, magnetic field generation coil unit 11U1 is disposed in a region in which x<xzh0, and magnetic field generation coil unit 11U2 is disposed in a region in which x>xzh0.

That is, a part of the conductive wire forming magnetic field generation coil units 11U1 and 11U2 is disposed in a location in which the z axis direction magnetic field component is zero of the magnetic field formed by the power supply coil and the power reception coil.

With the above configuration, the direction of the z direction magnetic field of the power transmission coil and the direction of the magnetic field of the magnetic field generation coil can be the same as each other in both regions, so that the z direction magnetic fields can strengthen each other in both regions and foreign matter detection sensitivity is improved.

Figure 13B:
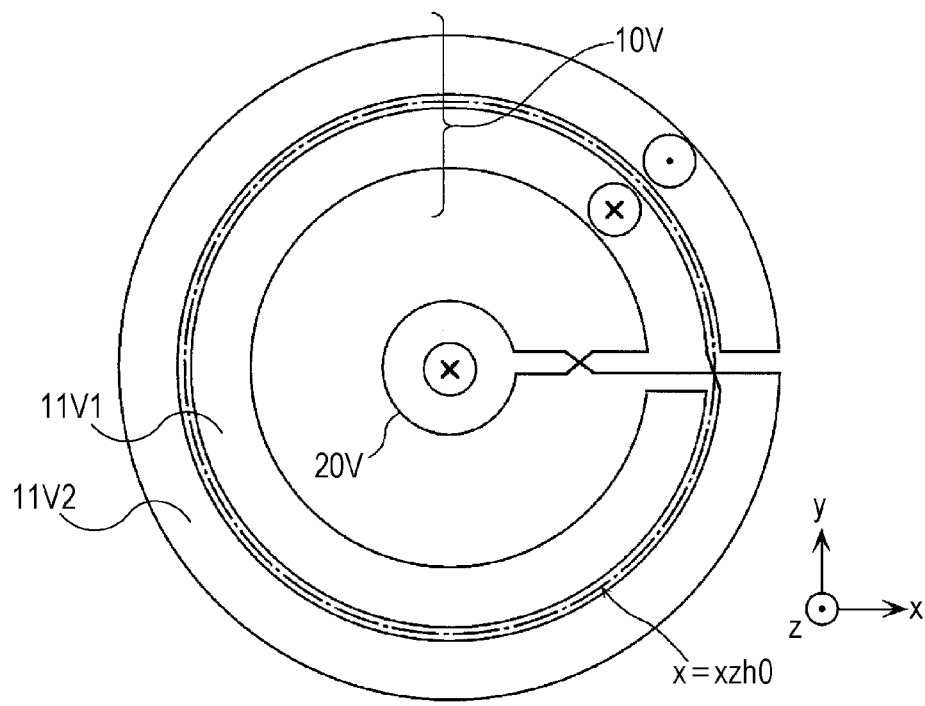
FIG. 13B is a plan view illustrating shapes of a magnetic field generation coil and a magneto coil according to a nineteenth modification of the exemplary embodiment.

FIG. 13B is a plan view illustrating shapes of a magnetic field generation coil and a magneto coil according to a nineteenth modification of the exemplary embodiment. FIG. 13B illustrates a configuration of magnetic field generation coil 10V and magneto coil 20V corresponding to a spiral type power transmission coil.

Magnetic field generation coil 10V has two magnetic field generation coil units 11V1 and 11V2 in which directions of the respective generated magnetic fields are opposite to each other. When x is a distance in the radial direction from the center and x=0 is the center of the power supply coil, magnetic field generation coil unit 11V1 is disposed in a region in which x<xzh0, and magnetic field generation coil unit 11V2 is disposed in a region in which x>xzh0.

That is, a part of the conductive wire forming magnetic field generation coil units 11V1 and 11V2 is disposed in a location in which the z axis direction magnetic field component is zero of the magnetic field formed by the power supply coil and the power reception coil.

With the above configuration, the direction of the z direction magnetic field of the power transmission coil and the direction of the magnetic field of the magnetic field generation coil can be the same as each other in both regions, so that the z direction magnetic fields can strengthen each other in both regions and foreign matter detection sensitivity is improved.

In FIG. 13A and FIG. 13B, the magnetic field generation coil and the magneto coil are formed electrically continuously (in a layout of one-stroke sketch); however, it is not limited thereto. The number of turns of each magnetic field generation coil unit may be two or more. The number of turns may be changed depending on strength of the z direction magnetic field. For example, when the number of turns is increased as the z direction magnetic field is weaker, the z direction magnetic field is leveled.

Foreign matter detection is preferably performed at timing when the time change amount of the magnetic field of the magnetic field generation coil is the peak value. From this, foreign matter detection sensitivity is improved. In other words, foreign matter detection is preferably performed at the time when the time change amount of the magnetic field of the power transmission coil is the peak value. Foreign matter detection is preferably performed at timing when the current of the power transmission coil is almost zero. From this, the magnetic field change amount generated by the magnetic field generation coil and magnetic field change amount generated by the power transmission coil strengthen each other. Accordingly, foreign matter detection sensitivity is improved.

The magnetic field by the magnetic field generation coil is generated also in the outside of the magnetic field generation coil.

In FIG. 13A, the direction of the z direction magnetic field of magnetic field generation coil unit 11U1 in the left side and the direction of the z direction magnetic field in the left outside of the unit are opposite to each other. The direction of the z direction of magnetic field generation coil unit 11U2 in the right side and the direction of the z direction magnetic field in the right outside of the unit are opposite to each other.

In FIG. 13B, the direction of the z direction magnetic field of magnetic field generation coil unit 11V1 in the inner side and the direction of the z direction magnetic field in a region being in the circle center side of magnetic field generation coil unit 11V1 are opposite to each other. The direction of the z direction magnetic field of magnetic field generation coil unit 11V2 in the outer side and the direction of the z direction magnetic field in a region being an outer circumferential side of magnetic field generation coil unit 11V2 are opposite to each other.

In the above description, attention is paid to the direction of the z direction magnetic field of the inside of the magnetic field generation coil; however, when the direction of the z direction magnetic field of the outside of the magnetic field generation coil unit and the direction of the z direction magnetic field of the power transmission coil weaken each other, foreign matter detection sensitivity degrades, and it is not preferable.

From this viewpoint, in FIG. 13A and FIG. 13B, the current direction of the magnetic field generation coil may be inverted and foreign matter detection may be performed with a current condition of each direction. For this purpose, it is sufficient that switches are provided between the magneto coil and the magnetic field generation coil to switch the current directions by turning on/off the switches.

However, addition of the switches, or addition of a function of changing the current direction causes a cost increase. Therefore, when the current is not caused to flow through the magnetic field generation coil, it is possible to eliminate that the magnetic fields weaken each other in the region of the outside of the magnetic field generation coil. That is, it is sufficient that foreign matter detection is performed in two cases, the case in which the current is caused to flow through the magnetic field generation coil, and the case in which the current is not caused to flow. This detection method can be applied also in the configurations illustrated in FIG. 2 and FIG. 12. The magnetic field generation coil may be a combination of those of FIG. 2 and FIG. 13A. The magnetic field generation coil may be a combination of those of FIG. 12 and FIG. 13B.

Figure 14A:
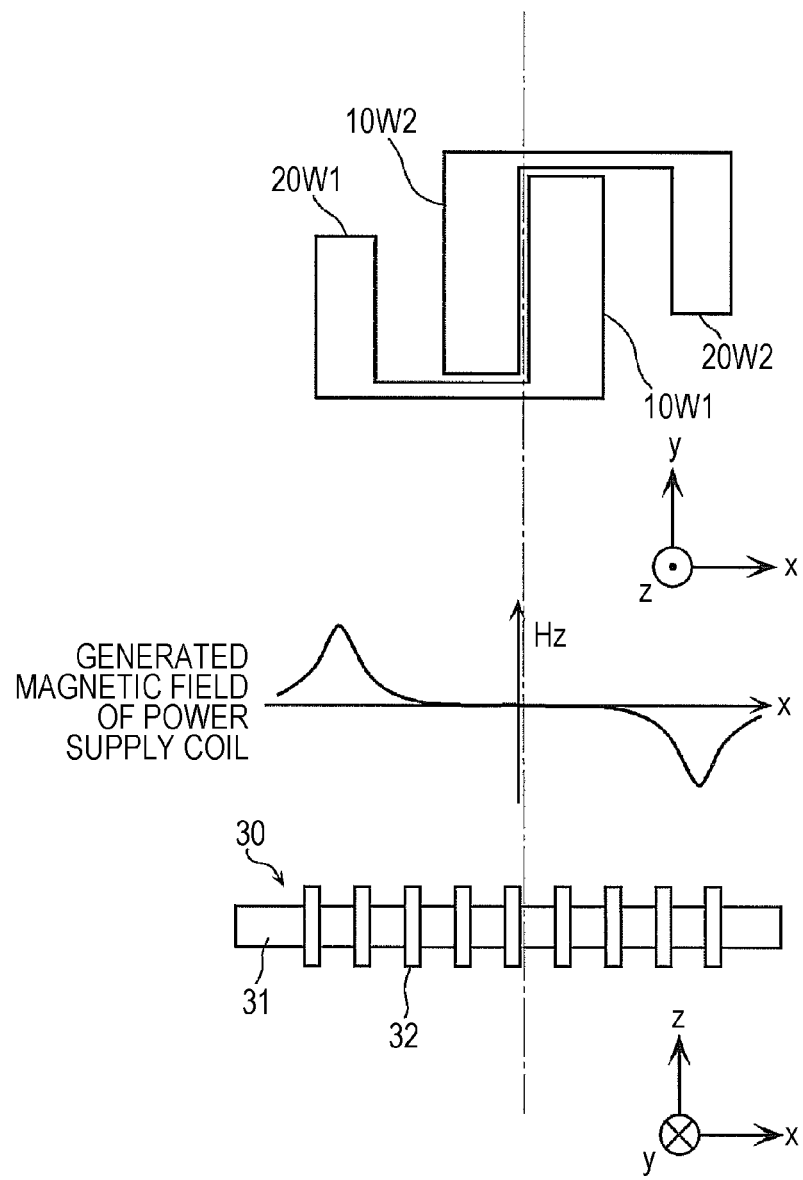
FIG. 14A is a plan view illustrating shapes of a magnetic field generation coil and a magneto coil according to a twentieth modification of the exemplary embodiment.

FIG. 14A is a plan view illustrating shapes of a magnetic field generation coil and a magneto coil according to a twentieth modification of the exemplary embodiment. FIG. 14A illustrates an arrangement relationship between magnetic field generation coil 10W1 connected to magneto coil 20W1 and magnetic field generation coil 10W2 connected to magneto coil 20W2, and illustrates a configuration example of when the magneto coil and the magnetic field generation coil are formed on the same substrate.

The configuration example represented in FIG. 14A is suitable for a case in which the power transmission coil is a solenoid type coil, and is a configuration example of when power is generated by the magneto coil using the magnetic field of the solenoid type coil.

The configuration of FIG. 14A is a configuration in which two sets are provided each of which is configured by one magneto coil and one magnetic field generation coil, and foreign matter detection is performed. In one set, magneto coil 20W1 is disposed at the left side of the solenoid coil, and magnetic field generation coil 10W1 is disposed to be in contact with the central portion of the solenoid coil, at the right side of the central portion. In the other set, magneto coil 20W2 is disposed at the right side of the solenoid coil, and magnetic field generation coil 10W2 is disposed to be in contact with the central portion of the solenoid coil, at the left side of the central portion. Two magnetic field generation coils 10W1 and 10W2 are adjacent to each other, and their boundary line is the central portion of the solenoid coil, and the boundary line is a region on which the z direction magnetic field is zero or near zero. As for the size of each of two magnetic field generation coils 10W1 and 10W2, a size is required capable of covering a region in which foreign matter detection sensitivity is low since the z direction magnetic field of the solenoid coil is small. The configuration of FIG. 14A is suitable for a case in which a main component of impedance of the magnetic field generation coil is an inductance component.

The middle part of FIG. 14A illustrates the distribution of the z direction magnetic field of the solenoid coil. Directions of the z direction magnetic fields of the left half and the right half are opposite to each other. From the principle of electromagnetic induction, the phase of the current to be caused to flow through the magnetic field generation coil is determined depending on the electromotive force generated by magneto coil 20W1 disposed at the left side. The direction of the magnetic field by the current coincides with the phase of the magnetic field of the right side of the solenoid coil. Therefore, in a case magneto coil 20W1 is disposed to the left, the magnetic field generation coil 10W1 connected to the magneto coil is preferably disposed at the right side. By coincidence of the phases of the magnetic fields, the z direction magnetic field can be increased by a scalar sum of the z direction magnetic field generated by the solenoid coil and the z direction magnetic field generated by the magnetic field generation coil. Accordingly, foreign matter detection sensitivity can be improved. In a case of magneto coil 20W2 disposed at the right side, from the same principle, magnetic field generation coil 10W2 connected to the magneto coil is preferably disposed at the left side. From this, the direction of the magnetic field of magnetic field generation coil 10W2 and the direction of the magnetic field of the solenoid coil in a region in which the magnetic field generation coil is disposed become the same as each other.

In a case the impedance of the magnetic field generation coil is dominated by a resistance component, from the principle of electromagnetic induction, the phase of the magnetic field of the magnetic field generation coil and the phase of the magnetic field of the solenoid coil cannot be caused to coincide with each other, and a phase difference of $\pi/2$ is generated between both phases.

Figure 14B:
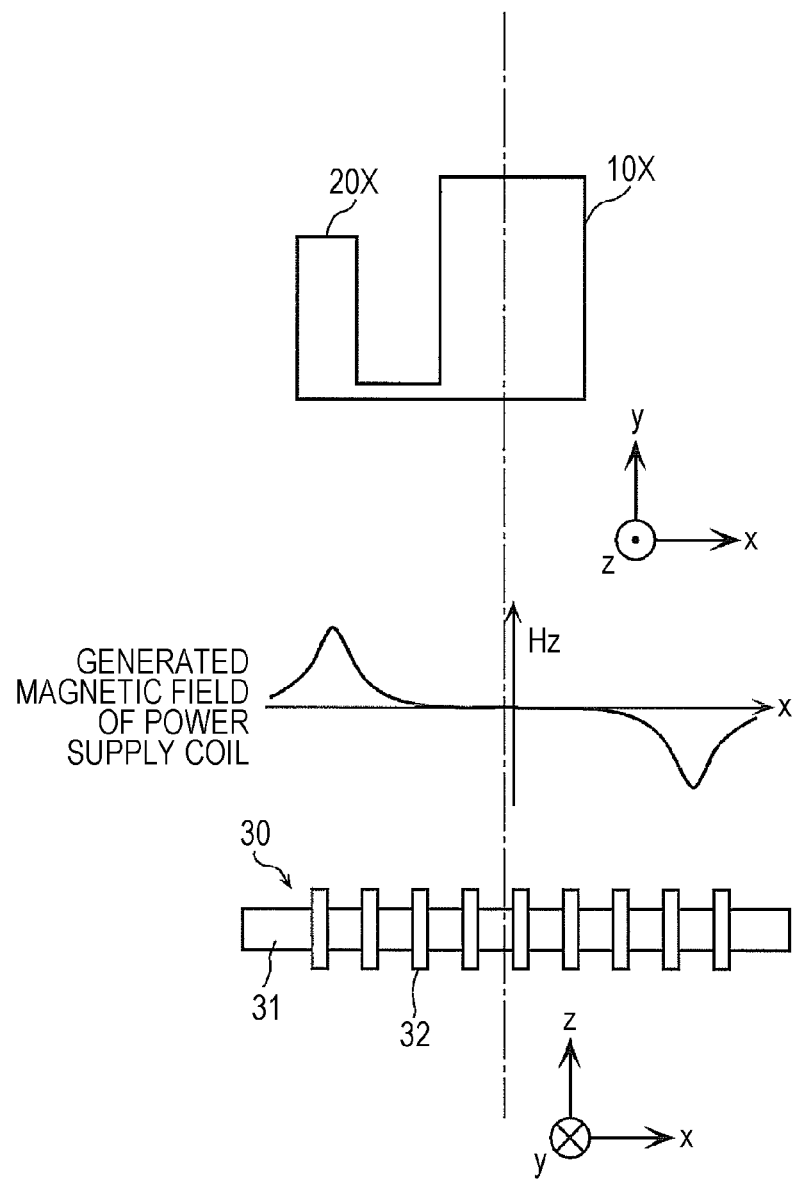
FIG. 14B is a plan view illustrating shapes of a magnetic field generation coil and a magneto coil according to a twenty-first modification of the exemplary embodiment.

FIG. 14B is a plan view illustrating shapes of a magnetic field generation coil and a magneto coil according to a twenty-first modification of the exemplary embodiment. FIG. 14B illustrates magnetic field generation coil 10X connected to magneto coil 20X, and illustrates a configuration example of when the magneto coil and the magnetic field generation coil are formed on the same substrate. In a case the phase difference is $\pi/2$ between the magnetic field of the magnetic field generation coil and the magnetic field of the solenoid coil, one magnetic field generation coil 10X is sufficient. It is sufficient that magnetic field generation coil 10X is disposed in a form of covering a region in which the z direction magnetic field is small, to cover the central portion in the x direction of the solenoid coil.

In this way, even in a case the main component of the impedance of the magnetic field generation coil is resistance, a similar effect can be obtained as the effect obtained by the configuration of FIG. 14A.

In the configuration of FIG. 14A, there are two sets of the magneto coil and the magnetic field generation coil, and in the configuration of FIG. 14B, there is one set of the magneto coil and the magnetic field generation coil. Accordingly, the configuration of FIG. 14B has less number of sets and better area efficiency. That is, in a case the main component of the impedance of the magnetic field generation coil is the resistance component, the configuration of FIG. 14B is desirable.

Since loss is increased when the resistance component of the magnetic field generation coil is increased, the resistance component is desirably as small as possible. That is, the main component of the impedance of the magnetic field generation coil is desirably the inductance component, and from this viewpoint, the configuration of FIG. 14A is more desirable than the configuration of FIG. 14B.

In a case both components have to be considered of the inductance component and the resistance component as the impedance component of the magnetic field generation coil, the configuration of FIG. 14A is desirable. This is because, in a case of the configuration of FIG. 14A, each combined magnetic field of the z direction magnetic field of the magnetic field generation coil and the z direction magnetic field of the solenoid coil has the same magnitude. In a case of the configuration of FIG. 14B, since magnitudes of the combined magnetic fields are different from each other between the right side and the left side in the magnetic field generation coil, a difference occurs in foreign matter detection sensitivity and the sensitivity cannot be leveled.

The number of turns of the magneto coil may be two or more, and the number of turns of the magnetic field generation coil may be two or more.

Figure 14C:
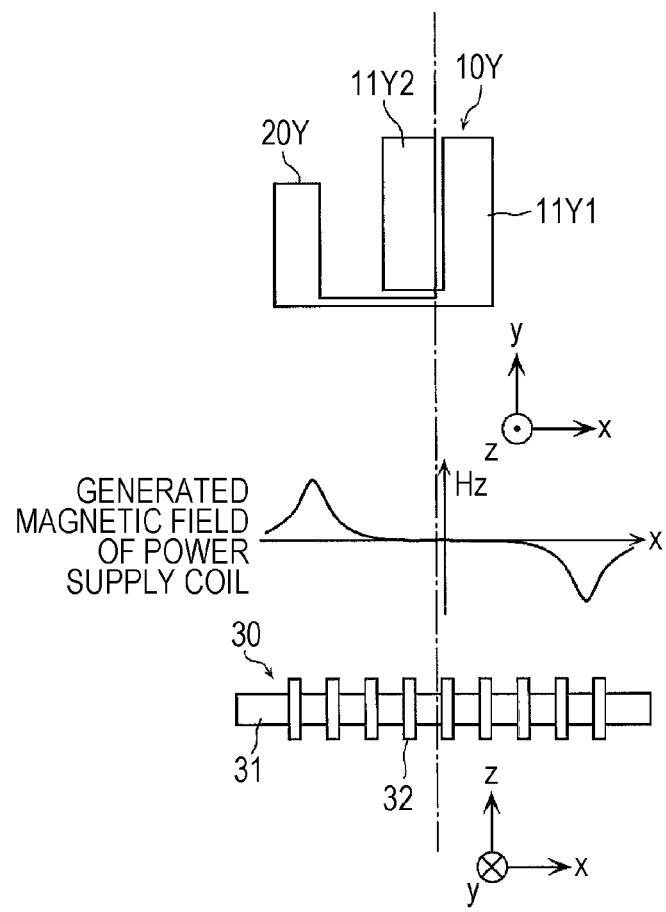
FIG. 14C is a plan view illustrating shapes of a magnetic field generation coil and a magneto coil according to a twenty-second modification of the exemplary embodiment.

FIG. 14C is a plan view illustrating shapes of a magnetic field generation coil and a magneto coil according to a twenty-second modification of the exemplary embodiment. FIG. 14C illustrates magnetic field generation coil 10Y connected to magneto coil 20Y, and illustrates a configuration example of when the magneto coil and the magnetic field generation coil are formed on the same substrate. The configuration of FIG. 14C is an example modified from that of FIG. 14A. Magnetic field generation coil 10Y has magnetic field generation coil units 11Y1 and 11Y2 for respectively generating magnetic fields of opposite directions to each other. Since the phase is $\pi$ between two magnetic field generation coils 10W1 and 10W2 of FIG. 14A, as illustrated in FIG. 14C, the magneto coil can be reduced to one from two by providing magnetic field generation coil units 11Y1 and 11Y2 respectively having opposite current directions to each other of the magnetic field generation coils.

Figure 14D:
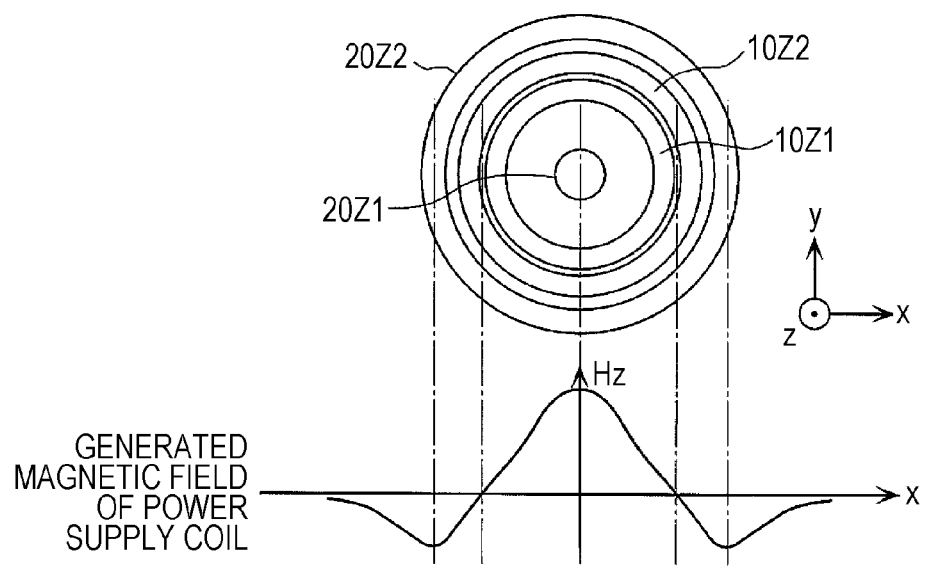
FIG. 14D is a plan view illustrating shapes of a magnetic field generation coil and a magneto coil according to a twenty-third modification of the exemplary embodiment.

FIG. 14D is a plan view illustrating shapes of a magnetic field generation coil and a magneto coil according to a twenty-third modification of the exemplary embodiment. The configuration illustrated in FIG. 14D is an example representing an arrangement configuration of the magneto coil and the magnetic field generation coil of when the power transmission coil is a spiral type coil. In FIG. 14D, circular magneto coil 20Z1 is disposed at the circle center portion, magneto coil 20Z2 is disposed at the outermost circumferential portion, and two magnetic field generation coils 10Z1 and 10Z2 are disposed between magneto coils 20Z1 and 20Z2.

Here, the boundary between magnetic field generation coils 10Z1 and 10Z2 is a region in which the z direction magnetic field created by the power transmission coil is zero or small. The magnetic field generation coil forming a set with magneto coil 20Z1 in the circle center portion is magnetic field generation coil 10Z2 in the outer side of the two magnetic field generation coils. The magnetic field generation coil forming a set with magneto coil 20Z2 in the outermost circumferential portion is magnetic field generation coil 10Z1 in the inner side of the two magnetic field generation coils.

With the above configuration, in the configuration of FIG. 14D applied to the spiral coil, the concept in the configurations of FIG. 14B and FIG. 14C applied to the solenoid coil can be applied similarly, and a similar effect can be obtained.

[6. Arrangement Relationship Between Magnetic Field Generation Coil and Sensor Coil]

In the following, an arrangement relationship between the magnetic field generation coil and the sensor coil is described.

Figure 15:
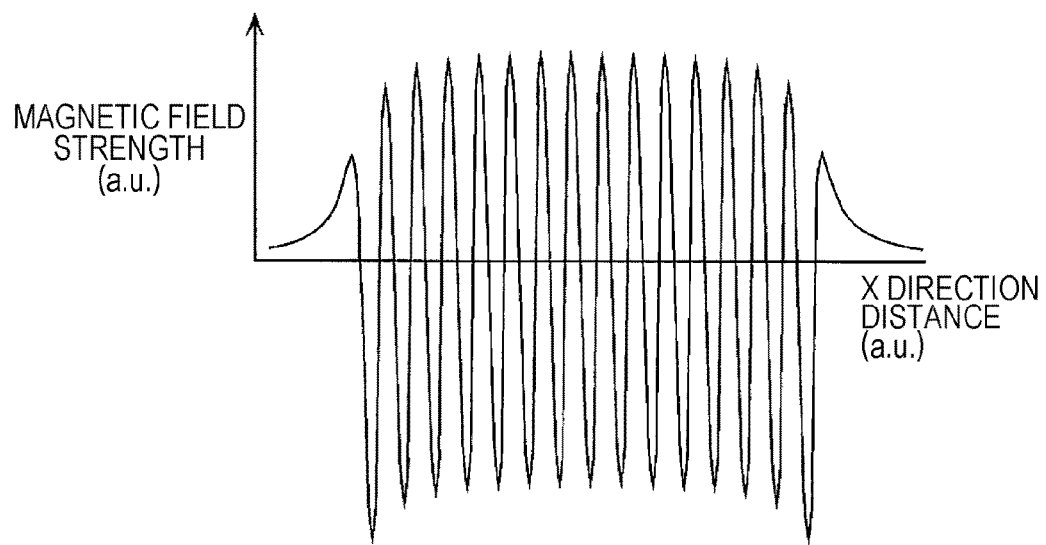
FIG. 15 is a graph representing a magnetic field distribution generated by a magnetic field generation coil including a plurality of rectangular magnetic field generation coil units.

FIG. 15 is a graph representing a magnetic field distribution generated by a magnetic field generation coil including a plurality of rectangular magnetic field generation coil units. More specifically, FIG. 15 represents a distribution in the x direction of the z direction magnetic field generated by the above magnetic field generation coil. The above magnetic field distribution is the distribution of the z direction magnetic field in a location apart about 10 mm in the z direction from the magnetic field generation coil.

In the magnetic field distribution illustrated in FIG. 15, it can be seen that the plus peak is decreased and the absolute value of the minus peak is increased in regions of both ends in the x direction of the magnetic field generation coil array. That is, a case is assumed in which the magnetic field to be generated is not uniform depending on the location of the sensor coil unit. Foreign matter detection sensitivity is reduced when the absolute value of the magnetic field is reduced. On the other hand, the magnetic field of the central region in the x direction tends to be uniform.

From the above magnetic field distribution, it is not preferable to perform foreign matter detection in the end regions of the magnetic field generation coil array. As a countermeasure, it is sufficient that the region in the x direction of the sensor coil array is caused to coincide with the region where generated magnetic field is stable, excluding the ends of the magnetic field generation coil array. For example, it is sufficient that one or more magnetic field generation coil units are disposed outside the region in the x direction of the sensor coil array.

Figure 16:
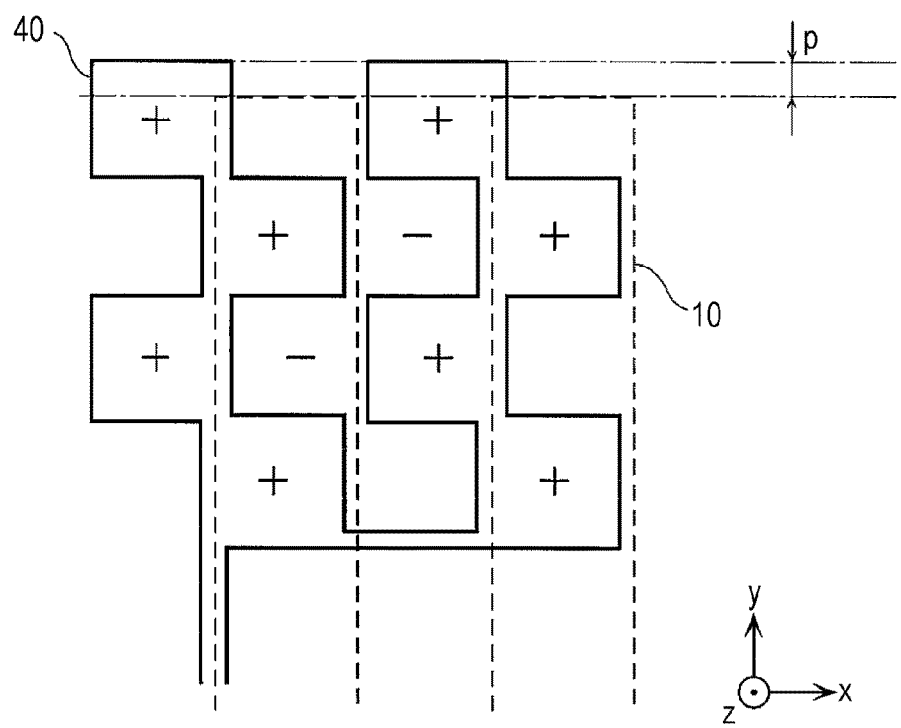
FIG. 16 is a plan view representing an arrangement relationship between the magnetic field generation coil and a sensor coil according to the exemplary embodiment.

FIG. 16 is a plan view representing an arrangement relationship between the magnetic field generation coil and a sensor coil according to the exemplary embodiment. FIG. 16 illustrates a positional relationship between magnetic field generation coil 10 and sensor coil 40 in which a plurality of sensor coil units is formed electrically in series and contiguously (in a layout of one-stroke sketch). Sensor coil 40 is an example of having four columns of sensor coil units in the x direction and four rows of sensor coil units in the y direction. Two types of the sensor coil units, a plus sensor coil unit indicated by + and a minus sensor coil unit indicated by −, are created. The plus and minus of the sensor coil units represent signs of voltages appearing at the output terminals of sensor coil 40 when a uniform magnetic flux change is applied to the sensor coil. A sum of electromotive forces of the plus sensor coil units and the minus sensor coil units is output to the output terminal. In FIG. 16, there are eight plus sensor coil units and two minus sensor coil units; the numbers of both units do not coincide with each other, and there is a difference of six. When all magnetic fields passing through the sensor coil units are the same as each other, since the electromotive forces of two plus sensor coil units and the electromotive forces of two minus sensor coil units cancel each other and the electromotive forces contributing the output voltage is 0 V, the electromotive forces contributing the output voltage is only the electromotive forces of six plus sensor coil units of the above difference. Since sensor coil 40 determines presence of foreign matter by measuring an amount of change in the output voltage between when the foreign matter exists and when the foreign matter does not exist, the S/N ratio can be increased as the absolute value of an output voltage V0 of when the foreign matter does not exist is closer to 0 V, so that foreign matter detection sensitivity can be improved. However, when the sensor coil is formed in a layout of one-stroke sketch, the numbers of the plus sensor coil units and the minus sensor coil units do not coincide with each other, in principle. The reason is that, as can be seen from FIG. 16, in the most peripheral portion of sensor coil 40, only the plus sensor coil units are formed and the minus sensor coil units are not formed. Therefore, there is a limit in bringing the output voltage close to 0 V of sensor coil 40 formed in one-stroke sketch.

To cope with this problem, as illustrated in FIG. 16, magnetic field generation coil 10 is laid over the region in which the sensor coil units are not formed, and the end of magnetic field generation coil 10 is disposed to the inner side by a distance p from the upper end sides of the plus sensor coil units in the left and right of the magnetic field generation coil. From this, the electromotive forces of the peripheral plus sensor coil units can be reduced. As a result, V0 can be brought further close to 0 V. The arrangement relationship between the magnetic field generation coil and the circular and donut-shaped sensor coils, which are suitable for the spiral type coil, can be a similar relationship.

Figure 17:
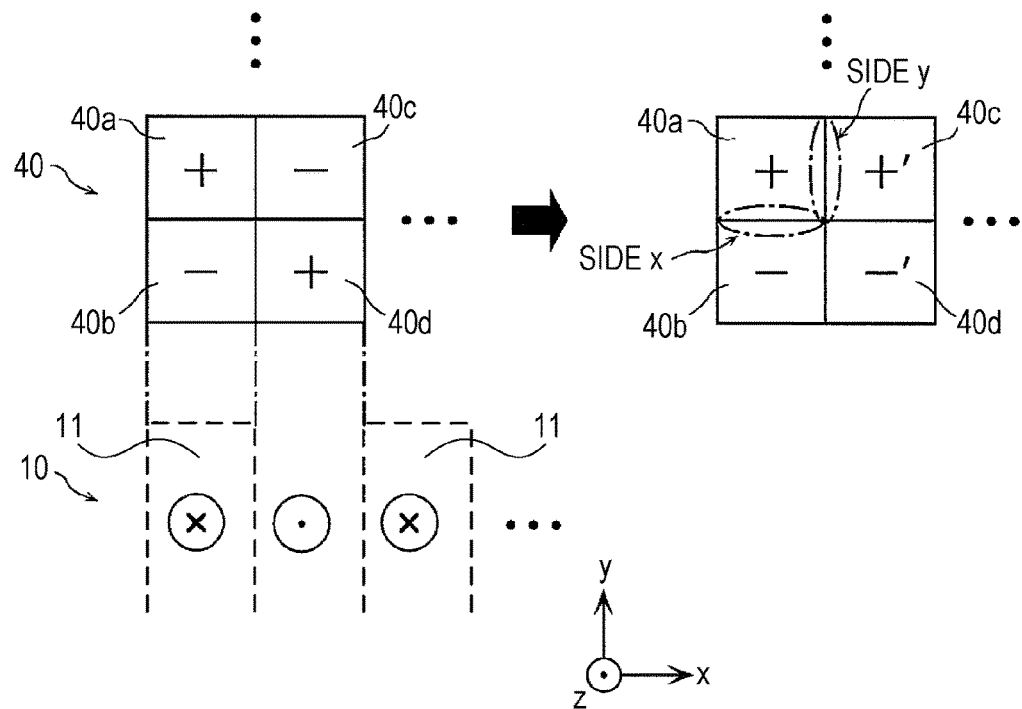
FIG. 17 is a diagram explaining a first relationship between a sign of the sensor coil and direction of a generated magnetic field of the magnetic field generation coil.

FIG. 17 is a diagram explaining a first relationship between a sign of the sensor coil and a direction of a generated magnetic field of the magnetic field generation coil. Although there are many sensor coil units in some cases, here, a case of four sensor coil units is described.

As illustrated in the left side of FIG. 17, four sensor coil units 40a to 40d are disposed such that signs of adjacent sensor coil units are opposite to each other. Here, the length of the side in the x direction of the sensor coil unit and the length of the width in the x direction of magnetic field generation coil unit 11 are substantially the same as each other, and sensor coil 40 and magnetic field generation coil 10 are disposed vertically (z direction) such that wiring lines extending in the y direction of both units overlap each other. The signs of the sensor coil units are determined depending on the way of taking the layout and their wire connections. Here, when directions of all magnetic fields passing through the sensor coil units are the same as each other, the sign of the sensor coil unit coincides with the sign of the electromotive force of the sensor coil unit.

In a case of an arrangement configuration illustrated in the left side of FIG. 17, the directions of the magnetic fields are different from each other depending on the locations of the sensor coil units. In this case, the sign of the electromotive force is determined depending on logic of the sign of the sensor coil unit and the magnetic field direction.

The right side of FIG. 17 illustrates the signs of the electromotive forces of the sensor coil units 40a to 40d. Here, the sign of the electromotive force of the sensor coil unit positioned in the generated magnetic field toward the back direction of the magnetic field generation coil unit 11 is defined to coincide with the sign of the sensor coil unit. When the sign of the sensor coil unit and the sign of the electromotive force do not coincide with each other, a prime is added to the sign, as +', or −'.

The signs of the electromotive forces of the sensor coil units 40*a* and 40*b* coincide with the signs of the respective sensor coil units. On the other hand, it can be seen that the signs of the electromotive forces of the sensor coil units 40*c* and 40*d* are opposite to the signs of the respective sensor coil units.

Here, attention is paid to sensor coil unit 40*a*, and a case is considered in which foreign matter exists at a side y in the y direction and a side x in the x direction. When directions of all magnetic flux passing through the sensor coil units are the same as each other, the sign of the electromotive force of the sensor coil unit becomes the same as the sign of sensor coil 40. Since the signs of the electromotive forces of adjacent sensor coil units are opposite to each other, foreign matter detection sensitivity degrades in a case foreign matter exists on the side that is the boundary between adjacent sensor coil units. The reason is that, in two sensor coil units having the boundary that is the side on which the foreign matter exists, absolute values of amounts of change in the electromotive forces of the plus sensor coil unit and the minus sensor coil unit are the same level as each other, and the signs of voltages contributing the output voltages of both units are opposite to each other. From this, the amount of change in the electromotive force of the plus sensor coil unit and the amount of change in the electromotive force of the minus sensor coil unit respectively have directions that cancel each other.

However, as illustrated in the right side of FIG. 17, since sensor coil unit 40*c* has plus electromotive force, in a case the foreign matter exists on the side y, the change in the electromotive force of sensor coil unit 40*a* and the change in the electromotive force of sensor coil unit 40*c* do not respectively have directions that cancel each other, but have directions that increase each other. That is, detection sensitivity to the foreign matter on the side y is improved on the contrary. This means that, depending on the arrangement relationship between sensor coil 40 and magnetic field generation coil 10, detection sensitivity to the foreign matter on the side of the sensor coil unit can be significantly improved. On the other hand, in a case the above current line does not exist on the above boundary, since the z direction magnetic field is small, foreign matter detection sensitivity is low.

Next, a case is considered in which the foreign matter exists on the side x.

Figure 18:
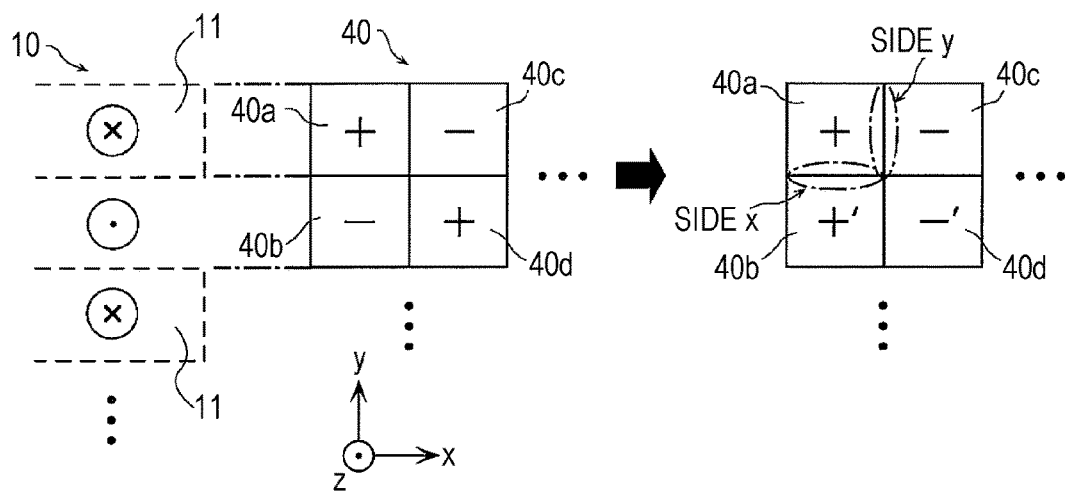
FIG. 18 is a diagram explaining a second relationship between the sign of the sensor coil and the direction of the generated magnetic field of the magnetic field generation coil.

FIG. 18 is a diagram explaining a second relationship between the sign of the sensor coil and the direction of the generated magnetic field of the magnetic field generation coil.

As illustrated in the right side of FIG. 18, since the sign of the electromotive force of sensor coil unit 40*a* is plus, and the sign of the electromotive force of sensor coil unit 40*c* is minus, changes in the electromotive forces work to cancel each other. As a result, foreign matter detection sensitivity on the side y is reduced. Since the directions of the magnetic fields passing through sensor coil unit 40*a* and sensor coil unit 40*c* are the same as each other, it is a natural result.

However, as illustrated in the right side of FIG. 18, since sensor coil unit 40*b* has plus electromotive force, in a case the foreign matter exists on the side x, the change in the electromotive force of sensor coil unit 40*a* and the change in the electromotive force of sensor coil unit 40*b* do not respectively have directions that cancel each other, but have directions that increase each other. That is, detection sensitivity to the foreign matter on the side x is improved on the contrary. This means that, depending on the arrangement relationship between sensor coil 40 and magnetic field generation coil 10, detection sensitivity to the foreign matter on the side of the sensor coil unit can be significantly improved.

Here, by having both the arrangement with magnetic field generation coil 10 illustrated in FIG. 17 and the arrangement with magnetic field generation coil 10 illustrated in FIG. 18, it is possible to generate different types of magnetic field distributions to perform foreign matter detection. From this, foreign matter detection sensitivity on the side is significantly improved.

That is, magnetic field generation coil substrate 110 has a first magnetic field generation coil unit (magnetic field generation coil unit 11 of FIG. 17) and a second magnetic field generation coil unit (magnetic field generation coil unit 11 of FIG. 18) each of which has conductive wire disposed along an outline of a rectangle. The first magnetic field generation coil unit and the second magnetic field generation coil unit are disposed to overlap each other in a normal line direction of a first plane and a second plane on magnetic field generation coil substrate 110 so that the first plane including the first magnetic field generation coil unit and the second plane including second magnetic field generation coil unit are parallel to each other. A long side of the first magnetic field generation coil unit and a long side of the second magnetic field generation coil unit are orthogonal to each other in a plan view (that is, when viewed from the above normal line direction).

Two magnetic field generation coils 10 described above may be separately driven, or may be simultaneously driven. A stronger magnetic field can be generated by simultaneously driving the coils, whereby foreign matter detection sensitivity is improved. At this time, by having two cases, the case in which the current directions of two magnetic field generation coils are the same as each other, and the case in which the current directions are opposite to each other, sensitivity of location dependence of foreign matter detection is made to be uniform.

Since the output voltage V0 of the sensor coil is a sum of all electromotive forces of the sensor coil units, it is necessary to bring the sum of all electromotive forces of the sensor coil units to be close to 0 V, in the configuration of FIG. 17 and FIG. 18. For example, the number of minus sensor coil units and the number of plus sensor coil units are made to be the same as each other, in which the sensor coil units are arranged in the y direction and have the same magnetic field directions generated by the magnetic field generation coil units. In this way, the number of minus sensor coil units and the number of plus sensor coil units can be caused to coincide with each other, in all of the sensor coil units configuring the sensor coil array.

The above is a description of the case in which the device is configured such that rectangular magnetic field generation coil units are arranged, and the number of magnetic field generation coil units in the y direction is one. On the other hand, in a case the device is configured to have a plurality of the magnetic field generation coil units in the y direction, or in a case the shape of the coil unit is other than a rectangle, detection sensitivity to the foreign matter on the side can be improved by applying the similar principle.

Figure 19:
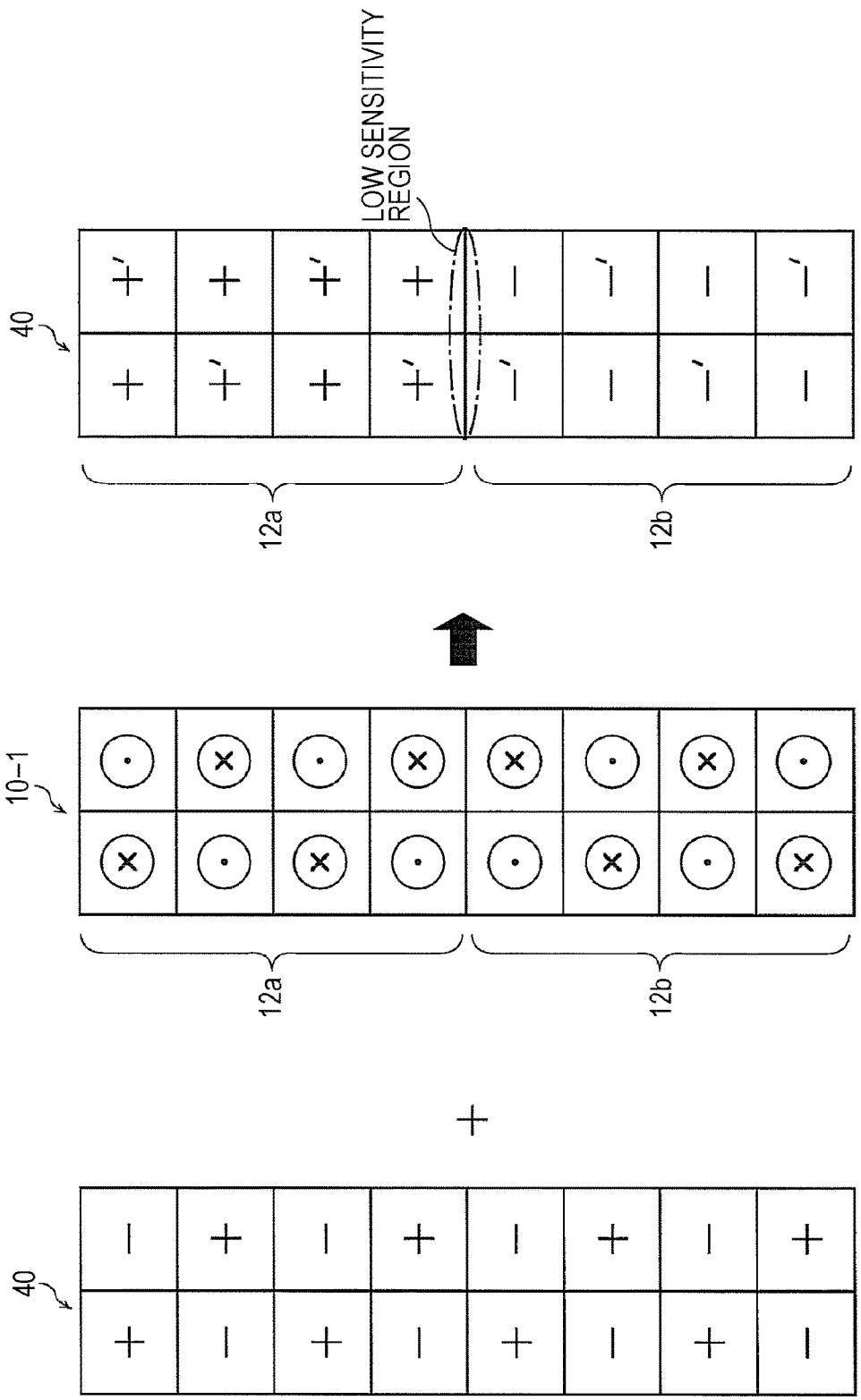
FIG. 19 is a diagram explaining a third relationship between the sign of the sensor coil and the direction of the generated magnetic field of the magnetic field generation coil.

FIG. 19 is a diagram explaining a third relationship between the sign of the sensor coil and the direction of the generated magnetic field of the magnetic field generation coil. The left side of FIG. 19 illustrates sensor coil 40 in which signs of adjacent sensor coil units are arranged to be opposite to each other. The center of FIG. 19 illustrates magnetic field generation coil 10-1. In magnetic field generation coil set 12a of the upper half, magnetic field generation coil units are arranged such that adjacent magnetic field directions are opposite directions to each other; in magnetic field generation coil set 12b of the lower half, the magnetic field generation coil set 12a vertically inverted is disposed. At a boundary between magnetic field generation coil sets 12a and 12b, magnetic field directions of the upper and lower magnetic field generation coil units sandwiching the boundary are the same directions as each other.

The sensor coil unit configuring sensor coil 40 and the magnetic field generation coil unit configuring magnetic field generation coil 10-1 have the same size.

The right side of FIG. 19 illustrates the signs of the electromotive forces of the sensor coil units obtained in a case sensor coil 40 and magnetic field generation coil 10-1 are disposed to overlap each other in the z axis direction with the sides aligned. The signs of the electromotive forces of the sensor coil units of the upper half are all plus, and the signs of the electromotive forces of the sensor coil units of the lower half are all minus. Here, since the number of plus electromotive forces and the number of minus electromotive forces are the same as each other, V0 can be brought close to 0 V.

When magnetic field directions of adjacent magnetic field generation coil units are reversely disposed in all of the magnetic field generation coil units, the electromotive forces of the sensor coil units are all plus, or minus. In this case, it is difficult to bring V0 close to 0 V. To avoid this, magnetic field directions of magnetic field generation coil set 12a of the upper side and magnetic field generation coil set 12b of the lower side are formed to be mirror-inverted to each other. Accordingly, the location in which detection sensitivity of the foreign matter on the side is reduced is only the boundary portion between magnetic field generation coil set 12a and magnetic field generation coil set 12b.

Figure 20:
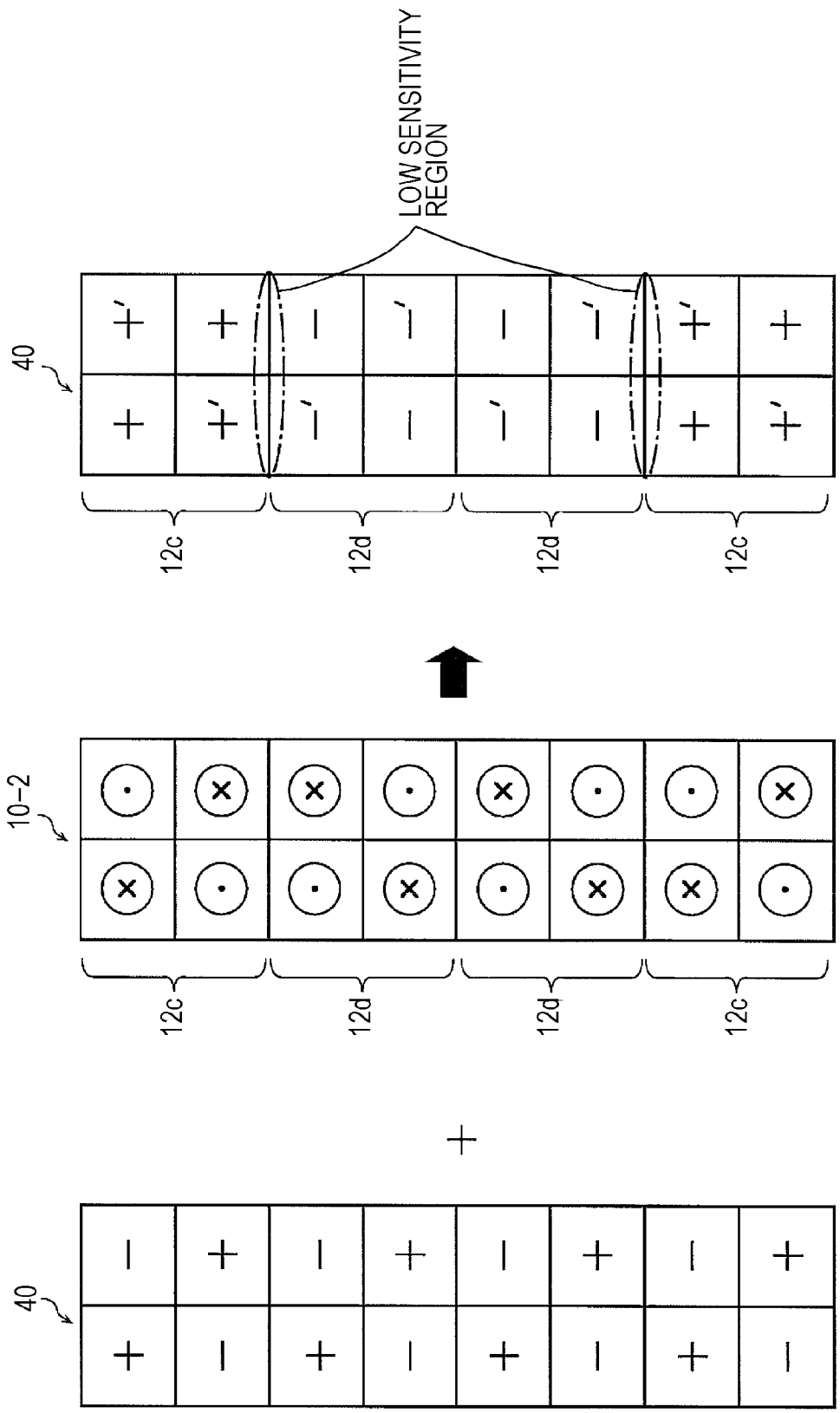
FIG. 20 is a diagram explaining a fourth relationship between the sign of the sensor coil and the direction of the generated magnetic field of the magnetic field generation coil.

FIG. 20 is a diagram explaining a fourth relationship between the sign of the sensor coil and the direction of the generated magnetic field of the magnetic field generation coil. The relationship between the signs of the sensor coils and directions of the generated magnetic fields of the magnetic field generation coils illustrated in FIG. 20 is the one modified from the above relationship of FIG. 19.

As illustrated in the center of FIG. 20, magnetic field directions of magnetic field generation coil sets 12c and 12d disposed at the upper half are vertically mirror-inverted, and magnetic field directions of magnetic field generation coil sets 12d and 12c disposed at the upper half are vertically mirror-inverted. In this case, as illustrated in the right side of FIG. 20, the sides on which foreign matter detection sensitivity is reduced are two locations, the boundary portion between magnetic field generation coil sets 12c and 12d in the upper half, and the boundary portion between magnetic field generation coil sets 12d and 12c in the lower half.

That is, by using both of magnetic field generation coil 10-1 illustrated in FIG. 19 and magnetic field generation coil 10-2 illustrated in FIG. 20, foreign matter detection sensitivity on the side can be improved.

Here, a method is described for using the magnetic field generation coil and using the magnetic field of the power transmission coil. As previously described, foreign matter detection sensitivity is improved as the magnetic field passing through the sensor coil is stronger. For this reason, when the magnetic field generated by the power transmission coil is used in addition to the magnetic field generated by the magnetic field generation coil, foreign matter detection sensitivity can be further improved. Exactly, when the time change amount of the magnetic field is increased, foreign matter detection sensitivity is improved. The time change amount of the magnetic field is maximized at timing when the magnetic field strength is zero in the magnetic field waveform of the power transmission coil. That is, it is sufficient to perform foreign matter detection when the magnetic field of the power transmission coil is close to zero.

From this viewpoint, by sensing the current of the power supply coil, the time may be predicted and foreign matter detection may be performed.

A search coil may be provided, and at timing when electromotive force of the search coil is maximized, foreign matter detection sensing may be performed. The timing is when the time change amount of the magnetic field of the power supply coil is maximized.

The directions of the magnetic fields of the magnetic field generation coil are different from each other depending on the magnetic field generation coil units, and the magnetic field created by the power transmission coil may have directions of when a time change amount of the magnetic flux is minus and when the time change amount is plus. For this reason, depending on the magnetic field generation coil unit, the direction of the magnetic field and the direction of the magnetic field of the power transmission coil are opposite directions to each other, and there may be a case in which strength of the combined magnetic field is reduced.

To solve this problem, when foreign matter detection is performed under the conditions of all combinations of the direction of the current to be caused to flow through the magnetic field generation coil and the sign of the time change amount of the magnetic field of the magnetic field generation coil, foreign matter detection sensitivity can be improved.

When foreign matter detection is performed while avoiding a period in which high-frequency noise is generated, reduction of the SN ratio due to the high-frequency noise can be avoided, and foreign matter detection sensitivity and accuracy can be improved.

There may be a case in which the magnetic field created by the power transmission coil changes or destabilizes V0 of the sensor coil, and foreign matter detection sensitivity and accuracy is reduced. At this time, there may be a case in which it is desirable to reduce influence of the magnetic field of the power transmission coil. As for an example of a method thereof, it is sufficient to perform foreign matter detection when the time change amount of the magnetic field of the power transmission coil is small, or is reduced. Specifically, it is timing when the magnetic field has a peak value. As for the timing, there are two timings, the timing of having a plus peak value in one period, and the timing of having a minus peak value. Foreign matter detection may be performed at either of the timings. In the above timings, the time change amount of the magnetic field is zero, so that influence to the sensor coil can be significantly reduced.

[7. Timing of Foreign Matter Detection]

Figure 21:
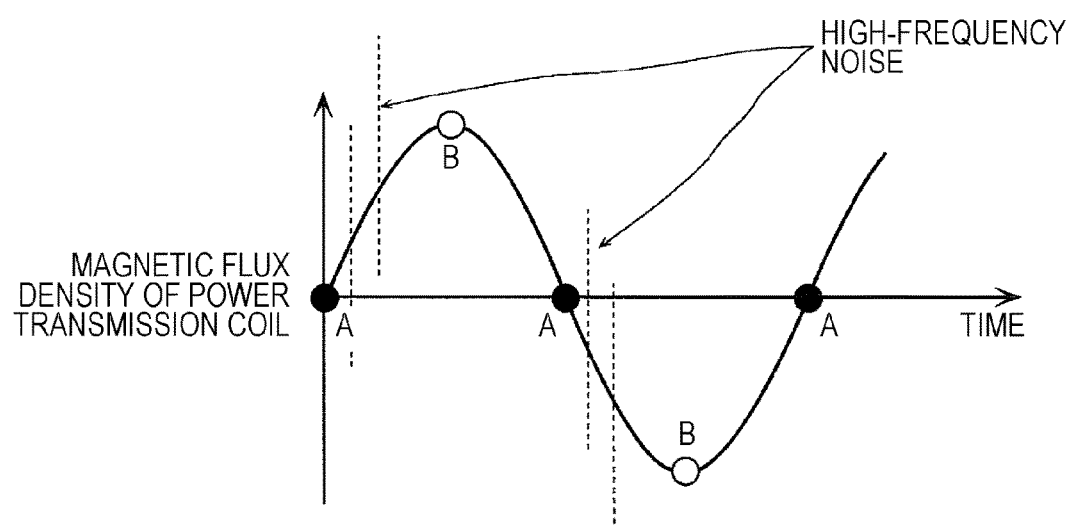
FIG. 21 is a conceptual waveform diagram representing a time change of a magnetic flux density generated by a power transmission coil.

FIG. 21 is a conceptual waveform diagram representing a time change of a magnetic flux density generated by a power transmission coil. Timing A illustrated in FIG. 21 is a time when the time change of the magnetic flux density is maximized. The drive circuit preferably drives the magnetic field generation coil at the timing A to execute foreign matter detection. From this, the magnetic field generated by the power transmission coil and the magnetic field generated by the magnetic field generation coil are superimposed together, and the magnetic field of a foreign matter detection space can be increased, so that foreign matter detection sensitivity can be improved.

The drive circuit may drive the magnetic field generation coil at timing B at which a magnetic flux change generated by the power transmission coil is small, to execute foreign matter detection. In a case foreign matter detection sensitivity is poor due to a low S/N ratio of the sensor coil, by doing the above, foreign matter detection sensitivity can be improved.

Detection of the timing A and timing B may be obtained by measuring current and voltage of the power transmission coil, may be obtained from timing of a gate signal of an inverter of a power transmission device, or may be obtained by providing a search coil and from a measurement value of electromotive force of the search coil.

The drive circuit may drive the magnetic field generation coil at timing of performing determination of presence of foreign matter 160. From this, since the magnetic field is intermittently generated, both of power consumption and electromagnetic radiation can be reduced.

The drive circuit may drive the magnetic field generation coil by changing at least one of the current, voltage, power and frequency of the power supply coil and the power reception coil. From this, the drive circuit and the power source for driving the magnetic field generation coil can be simplified, so that it is possible to achieve reliability improvement, weight and size reduction, and cost reduction by reducing the number of parts.

[8. Other Arrangements of Magnetic Field Generation Coil]

The magnetic field generation coil may be provided at a power reception unit side that is the secondary side. Specifically, phases of current flowing through the magnetic field generation coil of the primary side and current flowing through the magnetic field generation coil of the secondary side are adjusted such that the z direction magnetic field generated by the primary side magnetic field generation coil and the z direction magnetic field generated by the secondary side magnetic field generation coil strengthen each other. From this, the z direction magnetic field is increased, and foreign matter detection sensitivity is improved. In particular, detection sensitivity of the foreign matter existing in the space is improved rather than that existing on the road.

Power may be generated by using the magnetic field generation coil of the secondary side, and the power generated may be supplied to a load. From this, power generation efficiency can be improved.

A coupling coefficient between the magnetic field generation coil of the primary side and the power supply coil of the primary side is preferably smaller than a coupling coefficient between the power supply coil of the primary side and the power reception coil of the secondary side.

A coupling coefficient between the magnetic field generation coil of the primary side and the power reception coil of the secondary side is preferably smaller than the coupling coefficient between the power supply coil of the primary side and the power reception coil of the secondary side.

As for a degree of coupling between the magnetic field generation coil of the primary side and the power supply coil of the primary side, and a degree of coupling between the magnetic field generation coil of the primary side and the power reception coil of the secondary side, the ratios are both preferably less than 10%. When the above degree of coupling is greater than 10%, a problem may occur in power supply and demand from the power supply coil to the power reception coil.

Since the magnetic field generated by the magnetic field generation coil crosses the power transmission coil, electromotive force is generated in the power transmission coil. In other words, noise is generated in voltage and current of the power transmission coil due to the current of the magnetic field generation coil. This noise is not preferable. Accordingly, it is necessary to adjust the coupling coefficient to reduce the above noise.

Next, an arrangement relationship between the magneto coil and the magnetic field generation coil is described.

The magnetic field generation coil substrate on which the magneto coil and the magnetic field generation coil are formed is disposed in parallel to the sensor coil substrate. The interval therebetween is preferably reduced as much as possible. They are preferably disposed to be in contact with each other.

The magnetic field generation coil substrate on which the magneto coil and the magnetic field generation coil are formed is preferably disposed in parallel to the xy plane of the power transmission coil. The interval therebetween is preferably reduced as much as possible. They are preferably disposed to be in contact with each other.

Next, a positional relationship between the magnetic field generation coil substrate, sensor coil substrate, and power transmission coil is described. The sensor coil substrate is preferably disposed between the magnetic field generation coil substrate and the power transmission coil substrate. The magnetic field generation coil substrate may be disposed between the sensor coil substrate and the power transmission coil substrate.

Other Exemplary Embodiments

In the above, the foreign matter detection device according to the present invention has been described on the basis of the exemplary embodiment and modifications; however, the present invention is not limited to the above exemplary embodiment and modifications.

The numbers used above are all exemplified to specifically explain the present disclosure, and the present disclosure is not restricted to the numbers exemplified.

The materials of components illustrated above are all exemplified to specifically explain the present disclosure, and the present disclosure is not restricted to the materials exemplified. The connection relationship between the components is exemplified to specifically explain the present disclosure, and the connection relationship for achieving functions of the present disclosure is not limited thereto.

Non-contact power supply device 100 according to the above exemplary embodiment is a system for charging a battery of a vehicle side from the power supply coil disposed on the ground of a parking lot, and foreign matter detection device 1 is incorporated on the ground; however, the foreign matter detection device according to the present invention is not limited thereto. The non-contact power supply device may be a system that supplies power to the EV travelling (moving), and a foreign matter detection device for sensing foreign matter on the road.

Further, as long as not departing from the spirit of the present disclosure, various modifications subjected to modification to the present exemplary embodiment within a range in which those skilled in the art can come up with an idea, are included in the present disclosure.

INDUSTRIAL APPLICABILITY

The foreign matter detection device according to the present disclosure can be applied for a non-contact power supply system of a mobile body, and the like.

The invention claimed is:

1. A foreign matter detection device mounted on a non-contact power supply system that supplies power in a non-contact manner from a power supply unit to a power reception unit, the foreign matter detection device comprising:
   a magnetic field sensor for detecting an amount of magnetic flux that changes due to foreign matter existing between the power supply unit and the power reception unit; and
   a magnetic field generation unit that is provided separately from the power supply unit and the power reception unit, includes at least one magnetic field generation coil unit, and generates a magnetic field for driving the magnetic field sensor.

2. The foreign matter detection device according to claim 1, wherein
   the at least one magnetic field generation coil unit includes a plurality of magnetic field generation coil units, and
   at least two of the plurality of the magnetic field generation coil units are formed electrically in series and contiguously.

3. The foreign matter detection device according to claim 1, wherein
   the at least one magnetic field generation coil unit includes a plurality of magnetic field generation coil units, and
   the magnetic field generation unit further includes:
      a plurality of terminals for supplying current to each of the plurality of the magnetic field generation coil units; and
      a plurality of first switch elements each of which is provided between each of the plurality of the magnetic field generation coil units and each of the corresponding plurality of terminals, and selects whether or not to supply current to each of the plurality of the magnetic field generation coil units.

4. The foreign matter detection device according to claim 1, wherein
   the at least one magnetic field generation coil unit includes a plurality of magnetic field generation coil units, and
   the magnetic field generation unit further includes:
      a plurality of terminals for supplying current to each of the plurality of the magnetic field generation coil units; and
      a plurality of second switch elements each of which is provided between each of the plurality of the magnetic field generation coil units and each of the corresponding plurality of terminals, and changes a direction of current flowing through each of the plurality of the magnetic field generation coil units.

5. The foreign matter detection device according to claim 1, wherein
   the at least one magnetic field generation coil unit includes a plurality of magnetic field generation coil units, and
   each of the plurality of the magnetic field generation coil units is formed having conductive wire disposed along an outline of a rectangle or a circular ring, and
   a width of each of the plurality of the magnetic field generation coil units is 1.5 times or more and 2.5 times or less as wide as a distance between the foreign matter and a plane including the magnetic field generation coil unit, the width being a length of a short side of the rectangle or a width of the circular ring.

6. The foreign matter detection device according to claim 1, wherein
   the at least one magnetic field generation coil unit includes a plurality of magnetic field generation coil units,
   each of the plurality of the magnetic field generation coil units is disposed on a plane at constant intervals,
   the magnetic field sensor includes a plurality of sensor coil units for detecting an amount of magnetic flux that changes due to presence of the foreign matter, as a voltage signal, and
   a width in a first direction of each of the plurality of the magnetic field generation coil units equals a width in the first direction of each of the plurality of sensor coil units.

7. The foreign matter detection device according to claim 1, wherein
   the at least one magnetic field generation coil unit includes a plurality of magnetic field generation coil units,
   each of the plurality of the magnetic field generation coil units includes a first magnetic field generation coil unit and a second magnetic field generation coil unit each of which has conductive wire disposed along an outline of a rectangle,
   the first magnetic field generation coil unit and the second magnetic field generation coil unit are disposed to overlap each other in a normal line direction of a first plane and a second plane such that the first plane including the first magnetic field generation coil unit and the second plane including the second magnetic field generation coil unit are parallel to each other, and
   a long side of the first magnetic field generation coil unit and a long side of the second magnetic field generation coil unit are orthogonal to each other when viewed from the normal line direction.

8. The foreign matter detection device according to claim 1, wherein
   the non-contact power supply system includes the power supply unit having a power supply coil and the power reception unit having a power reception coil, and
   the magnetic field generation unit is disposed at a location in which a magnetic field component in a normal line direction of the plane including the at least one magnetic field generation coil unit is relatively small or zero, out of a magnetic field formed by the power supply coil and the power reception coil.

9. The foreign matter detection device according to claim 1, further comprising:
   the power supply unit having a power supply coil; and
   the power reception unit having a power reception coil,
   wherein a magnetic coupling coefficient between the magnetic field generation unit and the power supply coil, and a magnetic coupling coefficient between the magnetic field generation unit and the power reception coil are both 10% or less.

10. The foreign matter detection device according to claim 1, further comprising a drive circuit for driving the magnetic field generation unit.

11. The foreign matter detection device according to claim 10, wherein
the drive circuit drives the magnetic field generation unit such that a time differential value of current flowing through the magnetic field generation coil unit is 1 A/50 ns or more.

12. The foreign matter detection device according to claim 10, wherein
the drive circuit changes at least one of a temporal change amount and an absolute value of at least one of current, voltage, power, and frequency to be supplied to the magnetic field generation coil unit, to drive the magnetic field generation unit.

13. The foreign matter detection device according to claim 1, wherein
the magnetic field generation unit further includes a magneto coil, and
the magneto coil generates electromotive force by using a magnetic field generated by the power supply unit and the power reception unit, and supplies the electromotive force generated to the at least one magnetic field generation coil unit.

14. The foreign matter detection device according to claim 13, further comprising a drive circuit for driving the magnetic field generation unit,
wherein the electromotive force generated by the magneto coil is supplied to a circuit of the foreign matter detection device including the drive circuit.

15. The foreign matter detection device according to claim 13, wherein a part of conductive wire forming the magnetic field generation coil unit is disposed at a location in which the magnetic field component in the normal line direction of the plane including the magnetic field generation coil unit is zero, out of a magnetic field formed by the power supply unit and the power reception unit.

16. The foreign matter detection device according to claim 10, wherein the drive circuit drives the magnetic field generation unit at timing of performing determination of presence of the foreign matter.

17. The foreign matter detection device according to claim 10, wherein the drive circuit drives the magnetic field generation unit at timing when an absolute value of a change in the magnetic field formed by the power supply unit and the power reception unit is minimum.

18. The foreign matter detection device according to claim 10, wherein the drive circuit drives the magnetic field generation unit at timing when current of the power supply unit or the power reception unit is zero.

19. The foreign matter detection device according to claim 10, wherein the drive circuit drives the magnetic field generation unit while avoiding time when a high frequency magnetic field is generated from the power supply unit or the power reception unit.

20. The foreign matter detection device according to claim 10, wherein the drive circuit drives the magnetic field generation unit by changing at least one of current, voltage, power, and frequency of the power supply unit and the power reception unit.

* * * * *